(12) United States Patent
Dazzi et al.

(10) Patent No.: US 8,418,538 B2
(45) Date of Patent: Apr. 16, 2013

(54) HIGH FREQUENCY DEFLECTION MEASUREMENT OF IR ABSORPTION

(75) Inventors: A. Dazzi Dazzi, Les Ulis (FR); Clotilde Policar, Paris (FR); Kevin Kjoller, Santa Barbara, CA (US); Michael Reading, Norwich (GB); Konstantin Vodopyanov, San Jose, CA (US); Craig Prater, Santa Barbara, CA (US)

(73) Assignee: Anasys Instruments Inc., Santa Barbara, CA (US)

( * ) Notice: Subject to any disclaimer, the term of this patent is extended or adjusted under 35 U.S.C. 154(b) by 0 days.

(21) Appl. No.: 13/289,640

(22) Filed: Nov. 4, 2011

(65) Prior Publication Data

US 2012/0050718 A1 Mar. 1, 2012

Related U.S. Application Data

(63) Continuation of application No. 12/315,859, filed on Dec. 5, 2008, now Pat. No. 8,402,819, which is a continuation-in-part of application No. 11/803,421, filed on May 15, 2007, now Pat. No. 8,001,830.

(51) Int. Cl.
*G01B 5/28* (2006.01)
*G01Q 60/34* (2010.01)
*G01N 21/84* (2006.01)

(52) U.S. Cl.
USPC .................................. 73/105; 850/33; 850/38

(58) Field of Classification Search ............... 73/105; 850/21, 33, 38
See application file for complete search history.

(56) References Cited

U.S. PATENT DOCUMENTS

| | | | |
|---|---|---|---|
| 5,003,815 A | * | 4/1991 | Martin et al. .................. 73/105 |
| 6,530,266 B1 | * | 3/2003 | Adderton et al. .............. 73/105 |
| 2007/0220978 A1 | * | 9/2007 | Su et al. ........................ 73/632 |

OTHER PUBLICATIONS

Dazzi, A. et al., "Local Infrared Microspectroscopy With Subwavelength Spatial Resolution With an Atomic Force Microscope Tip Used as a Photothermal Sensor", Optics Letters, vol. 30, No. 18, Sep. 15, 2005, pp. 2388-2390.*

Dazzi, A. et al. "Subwavelength Infrared Spectromicroscopy Using an AFM as a Local Absorption Sensor", Infrared Physics & Technology, vol. 49, 2006, pp. 113-121.*

* cited by examiner

*Primary Examiner* — Daniel Larkin
(74) *Attorney, Agent, or Firm* — Mark Rodgers

(57) ABSTRACT

An AFM based technique has been demonstrated for performing highly localized IR spectroscopy on a sample surface. Significant issues as to size, cost of implementation, and repeatability/robustness of results exist in commercializing the technique. The invention addresses many of these issues thereby producing a version of the analytical technique that can be made generally available to the scientific community.

2 Claims, 24 Drawing Sheets

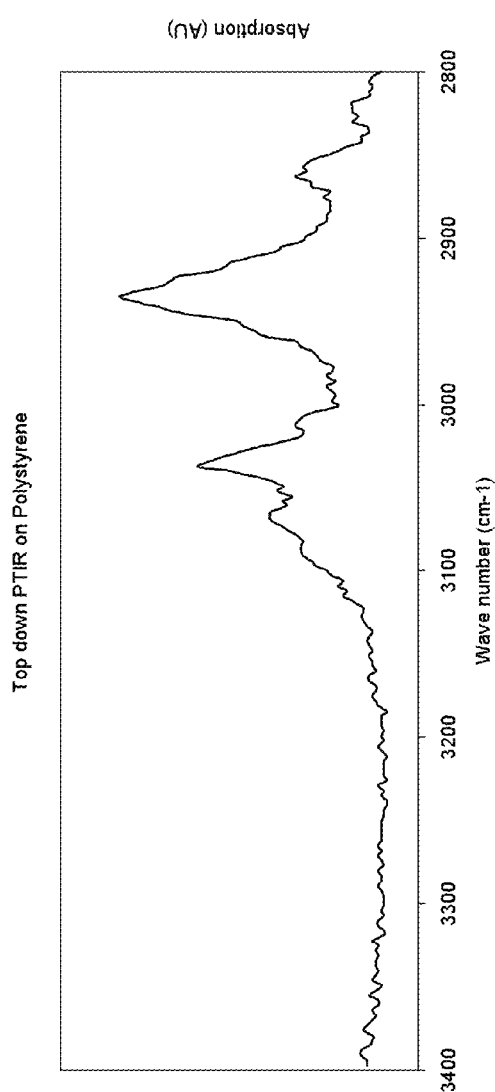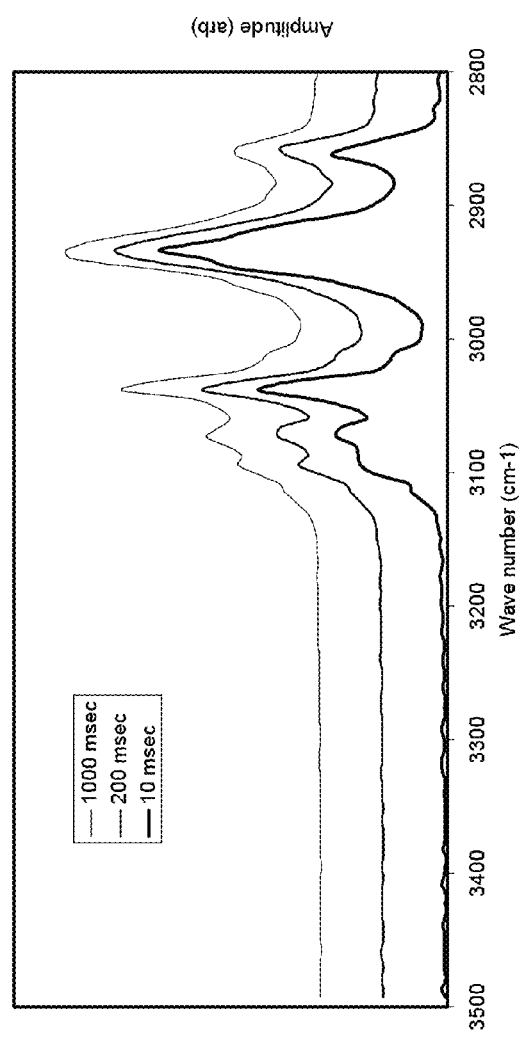

HIGH FREQUENCY DEFLECTION MEASUREMENT OF IR ABSORPTION

RELATED APPLICATIONS

This application is a Continuation of U.S. application Ser. No. 12/315,859, filed Dec. 5, 2008 which in turn is a Continuation-in-Part of U.S. application Ser. No. 11/803,421, filed May 15, 2007 now U.S. Pat. No. 8,001,830.

FEDERALLY SPONSORED RESEARCH

This invention was made with United States Government support under ATP Award 70NANB7H7025 awarded by the National Institute of Standards and Technology (NIST). The United States Government has certain rights in the invention.

SEQUENCE LISTING

Not Applicable

BACKGROUND OF THE INVENTION

This invention is related to highly localized Infrared (IR) spectra on a sample surface utilizing an Atomic Force Microscope (AFM) and a variable wavelength pulsed IR source.

IR spectroscopy is a useful tool in many analytical fields such as polymer science and biology. Conventional IR spectroscopy and microscopy, however, have resolution on the scale of many microns, limited by optical diffraction. It would be particularly useful to perform IR spectroscopy on a highly localized scale, on the order of biological organelles or smaller, at various points on a sample surface. Such a capability would provide information about the composition of the sample, such as location of different materials or molecular structures. Conventional infrared spectroscopy is a widely used technique to measure the characteristics of material. In many cases the unique signatures of IR spectra can be used to identify unknown material. Conventional IR spectroscopy is performed on bulk samples which gives compositional information but not structural information. Infrared Microscopy allows collection of IR spectra with resolution on the scale of many microns resolution. Near-field scanning optical microscopy (NSOM) has been applied to some degree in infrared spectroscopy and imaging. While there have been some promising laboratory results, there is still investigation and discovery required to enable a sensitive, and reliable commercial instrument. To our knowledge no widely available instrument provides routine IR spectra with resolution below the diffraction limit. Recently, one of the inventors has developed a technique based on use of an AFM in a unique fashion to produce such localized spectra. This work was described in a publication entitled "Local Infrared Microspectroscopy with Sub-wavelength Spatial Resolution with an Atomic Force Microscope Tip Used as a Photo-thermal Sensor" Optics Letters, Vo. 30, No. 18, Sep. 5, 2005. Those skilled in the art will comprehend the details of the technique in the publication but the technique will be described briefly herein for clarity. The general technique is also referred to as Photo-Thermal Induced Resonance, or PTIR.

Many AFM designs are known in the art, one common design is illustrated in FIG. 1. A cantilever with probe tip 2 is brought into proximity with a sample 3. As the probe tip interacts with the sample it influences the motion of the cantilever. This motion is often detected by a light beam 1 that is directed to the cantilever 2 which reflects the beam to a photo-detector 4. Deflection of the cantilever vertically due to interaction with the sample causes the beam spot to move on the detector, generating a difference signal from the detector quadrants. This type of AFM setup is called an optical lever arm, and commercially available AFMs using this technique can measure deflections of the lever on a sub-angstrom scale. Typically the photodetector is a 4-quadrant type, allowing motion of the vertical and lateral motions of the cantilever. Many other optical detection schemes have been employed including optical interferometry and diffraction. There are other options to detect the deflection of the cantilever that can alternately be used, such self sensing cantilevers that employ piezoresistive, piezoelectric, capacitive, and inductive readouts, for example. Any detection technique that is sensitive to the motion of the cantilever may be suitable. Preamplifiers and/or other signal conditioning electronics are often used to amplify the detector signal before data acquisition and processing. A scanner (not shown) is typically used to generate relative motion between the probe tip and sample. The scanner can create this motion by moving the sample, the probe tip or a combination of both. Scanners are typically made from one or more piezoelectric elements, but suitable scanners can also be made from actuators employing electrostatic, electrostrictive, magnetostrictive, inductive, voice coil and other motion mechanisms. Other actuators using other scanning mechanisms will also work as long as they can generate probe and/or sample motion over the scan ranges desired in response to an input signal. Often the scanners contain mechanical flexures to guide and or amplify the motion of the actuator. Feedback systems are typically employed to servo the sample and/or or tip up and down in response to height variations of the sample to maintain a desired interaction between the probe and the sample. This vertical servo signal vs. lateral position creates a topographical map of the surface which can achieve atomic resolution. A wide variety of variations of the AFM exist with different types of probes and so on for measurements other than topography. For instance, in a co-pending application by some of the inventors of this application, a version of an AFM configured to measure thermal properties of a surface is described.

The AFM set-up used for the published work on IR spectroscopy is shown schematically in FIG. 2. In this set-up, the sample 3 is mounted on a ZnSe prism, or prism made from other suitable materials, which does not absorb the radiation of interest. A pulsed IR source 9, in this case a Free Electron Laser beam, is directed into the prism. The prism is made at an angle such that the beam is in Total Internal Reflection in order for the beam to be propagative in the sample and evanescent in the air. Thus only the sample is significantly exposed to the laser radiation, and the AFM probe 2 is minimally exposed to beam 9. The Free Electron Laser (FEL) is an IR source that is both variable in wavelength and has a pulsed output. Free Electron Lasers are large expensive facilities, available at only a few institutions in the world. The FELs are also shared facilities such that each user only may access a limited amount of beam time per year. The probe 2 is placed at a point on the sample by the scanner 5 and is held at an average height by feedback electronics 6. Both the vertical and lateral deflection signal as well as the feedback signal, are may be monitored at 7.

Referring to FIG. 3, when the FEL is pulsed, the sample 3 may absorb some of the energy, resulting in a fast thermal expansion of the sample as shown in the Figure. This has the effect of a quick shock to the cantilever arm 2, which if the ability of the cantilever to respond to this shock is slower than the shock will result in exciting a resonant oscillation in the cantilever arm. The resonant oscillation decay or "cantilever ringdown" 12 is shown in FIG. 3. Because the absorbed energy is ideally contained within the sample, this shock is due primarily to rapid sample expansion as minimal IR energy is absorbed by the cantilever itself. Although the probe is kept in contact with the surface by the feedback electronics, the resonant signal is too fast for the feedback electronics, but can be observed directly from the photodetector 4. Thus the cantilever rings down in the manner shown in FIG. 3 while still in contact with the surface, an effect called "contact resonance". The absolute deflection, amplitude and frequency characteristics of the contact resonance vary with the amount of absorption as well as other properties, such as the local hardness, of the localized area around the probe tip, for example by analyzing the ringdown and/or the Fourier transform (FFT) 13 of the ringdown events. Also, depending on the direction of the expansion, vertical resonances, lateral resonances or both can be excited. If the tip is to the side of the absorbent material, this will typically cause a stronger lateral response in the cantilever. By repeating the above process at varying wavelengths of the FEL, an absorption spectra on a very localized scale is achieved. By scanning the probe to various points on the sample surface and repeating the spectra measurement, a map of IR spectral surface characteristics can be made. Alternatively, the wavelength of the FEL can be fixed at a wavelength that is characteristic of absorption of one of the components of the sample. The probe can then be scanned across the sample surface and a map of the location of that component can be generated.

Although the set-up as described produced positive results, there is no real possibility of commercializing the set-up as published. First, the IR light source used, the Free Electron Laser is a very large and expensive facility and only a few exist in the world. Alternative benchtop sources of IR radiation have been limited by one or more characteristics that have made them unsuitable for a widely available instrument. Picosecond OPO pulsed lasers have been used, but suffer from very high costs and low pulse repetition rates, often a few tens of Hz. Broadband IR sources like glowbars are sufficient for bulk IR spectroscopy, but have insufficient optical power density for micro and nanoscale applications unless used with unacceptably long acquisition and averaging times. $CO_2$ lasers have limited wavelength range and do not address a wide enough bandwidth to cover the "fingerprint region."

The apparatus described in the publications suffers from other limitations beyond the expensive and stationary IR source. The apparatus employs a bottoms-up illumination scheme that requires a sample to be placed on a specially fabricated IR transmitting prism. In addition to being costly and easy to damage, this arrangement requires special sample preparation techniques to prepare a sample thin enough such that the IR light can penetrate the sample to reach the probe. Further, the actual signals generated can be small thus requiring averaging of the signal and limiting the bandwidth of the technique. More sensitivity would be required to address a wider range of potential samples. Also, up to this point, the technique is not quantitative in terms of the amount of absorption that occurs in the local area. Determining the absorption from the contact resonance amplitude as well as the measurement of some thermal properties of the sample would improve the ability of the technique to identify materials. Thus a variety of issues must be addressed in order to take the published technique from a laboratory set-up to a commercial analytical instrument. The present invention addresses the commercialization issues.

BRIEF SUMMARY OF THE INVENTION

This invention is a novel benchtop instrument that can measure and map information about a sample's chemical composition with resolution down to the micron and nanometer scale. These measurements are enabled by a specialized Atomic Force Microscope (AFM) that provides highly localized Infrared (IR) spectra and absorption on a sample surface utilizing an Atomic Force Microscope (AFM). The instrument employs a benchtop source of variable wavelength infrared (IR) radiation that is broadly and continuously tunable over the "fingerprint region" that allows for highly sensitive discrimination and even identification of materials. (The fingerprint region has varying definitions in the literature, but covers wavelength ranges from roughly 7 to 17 um, with the richest region for chemical information being above 10 um.)

The system can be used to obtain IR spectra from highly localized regions of a sample, allowing discrimination and/or identification of the composition of a micro or nano-sized region of a sample. The system can also be used for mapping the variations in IR absorption over a wider area of a sample, by imaging the energy absorbed at one or more wavelengths. From these absorption maps, chemometric maps of a material can be created. Specifically, chemometric maps can indicate the localization of different materials by using localized IR absorption to assign a color, for example, to each major chemical component in an image.

The current invention enables the reproducible measurement of broadband infrared spectra at highly localized points on a sample using an apparatus that is both portable and affordable. It overcomes the key limitations of the prior art which provided either very narrow band spectra or required expensive and rare facilities like the Free Electron Laser, or had insufficient optical power density and/or modulation rates.

In one embodiment, the invention is an apparatus for measuring infrared absorption of a sample on a on a sub-wavelength scale employing a benchtop modulated source of IR radiation capable of producing infrared radiation over continuous wavelength range covering a significant fraction of the "fingerprint region." Light from the IR source is coupled to the sample and is tunable at a rate of greater than 1 cm-1/sec with a resolution of better than 32 cm-1. The light source can also be modulated at a repetition frequency in excess of 100 Hz. A probe with a tip interacts with the sample and responds to IR radiation absorbed by the sample. A detector measures the probe response, typically comprising a temperature change and/or induced probe motion, as a function of wavelength of the IR radiation.

In a related embodiment, the invention is a method of measuring a localized IR spectra of a sample which includes the steps of; illuminating the sample surface with a benchtop IR source that is tunable over a wavelength range overlapping the IR fingerprint region. Light from the IR source is focused on a region and pulsed periodically at rates in excess of 100 Hz. The sample in turn absorbs IR radiation from the pulse. The absorbed energy from the pulse raises the temperature of the sample and causes a resulting pulse of thermal expansion. An AFM cantilever or equivalent probe is placed at a point on the illuminated surface, collecting data from the probe due to the absorbed radiation. The data collected may be related to probe temperature, deflection, and/or resonant oscillation of the probe in response to the IR radiation absorbed by the sample. The invention further includes methods of discriminating and/or identifying materials on the basis of IR absorption of localized regions of a sample. It also includes methods of minimizing impacts from background IR absorption by regions not directly under the probe tip.

Spectra of IR absorption versus wavelength may also be generated at a variety of points on the surface by positioning the probe so as to make a spectral map of the surface. Alternatively, the entire deflection data may be taken at one or more points, and then the analysis of the amplitude and frequency characteristics may be selected later, possibly iteratively, to better observe the vertical or lateral deflection data of the cantilever in order to achieve the optimum resolution and discrimination of the spectra or different components of the sample. In some embodiments, a sign is given to the amplitude data indicative of the initial lateral displacement of the probe, which is useful to discriminate between the side of an absorbing material the probe is on. In other embodiments, the deflection data may be collected at one illumination wavelength of interest, rather than taking a spectra, at a variety of points on the sample.

In one embodiment, the instrument can measure spectra and/or absorption maps from almost arbitrary samples, employing a top-down illumination scheme that does not require any special sample preparation.

In one embodiment, the IR source comprises a pulsed optical parametric oscillator with a wavelength range from 2.5 um to more than 10 um.

In various embodiments, the system is designed to be easy to operate, with self-aligned, automated alignment and/or simplified alignment of the IR light source and the AFM probe on a desired region of interest of a sample. In this easy-to-use instrument, the IR source emission wavelength is computer controlled over a wide wavelength range, enabling rapid and automated scanning of a substantial fraction of the IR fingerprint region without user intervention.

In various embodiments, the invention also can automatically select appropriate modes of oscillation that are most sensitive to the motion of the sample induced by IR radiation of a region under the AFM tip. The invention can also suppress sources of background absorption that may otherwise compromise the measurement. The invention can also normalize the cantilever signals such that they diminish the impact of instrumental bias and thermomechanical properties of the sample other than IR absorption properties. As a result, the current invention can regenerate IR spectra that better match absorption spectra taken on conventional optical instruments. This process enables better matching of spectra to those existing in materials databases for accurate material identification.

In various embodiments, the invention is a system for measuring a localized IR spectra on a sample surface which includes a pulsed variable wavelength IR source, an AFM, typically consisting of a scanner, provision for mounting of the sample, a cantilever probe with a probe tip, and a cantilever deflection measurement capability. In some of these embodiments, the source is above or below the plane of the sample surface, so all or part of the cantilever probe may be of a material that is transparent to IR radiation so the probe is not affected by absorption itself, but only the sample absorbs energy. Transparent materials include silicon, sapphire, silver halides, heavy metal fluoride glasses and chalcogenide glasses. Alternatively, all or part of the cantilever is made to be reflective of IR radiation. Coating all or part of the cantilever with gold is one example of making the probe reflective. Alternatively the cantilever may be constructed entirely of an IR reflective material, for example gold. In certain other embodiments, the system includes a waveguide to direct energy from the source to the surface, thereby avoiding exposing the cantilever to radiation. In some embodiments, the cantilever may be the waveguide.

In other embodiments, the invention includes chemically tagging substances by chemically combining them with tags of know IR spectral behavior, and observing the tagged substances with a sub-micron scale IR absorption system, preferably a mapping system, in order to collect information such as the motion or identity of the tagged substance.

BRIEF DESCRIPTION OF THE DRAWINGS

The invention will be better understood by referring to the accompanying Figures.

FIG. 11 shows examples of IR absorption spectra obtained by the current invention. FIG. 11a shows an IR absorption spectrum obtained using the top down illumination embodiment of FIG. 7. FIG. 11b shows spectra acquired at different acquisition times, including measurements at 10 msec per data point.

DETAILED DESCRIPTION OF THE INVENTION

Photo Thermal Induced Resonance (PTIR) Overview

Figure 1:
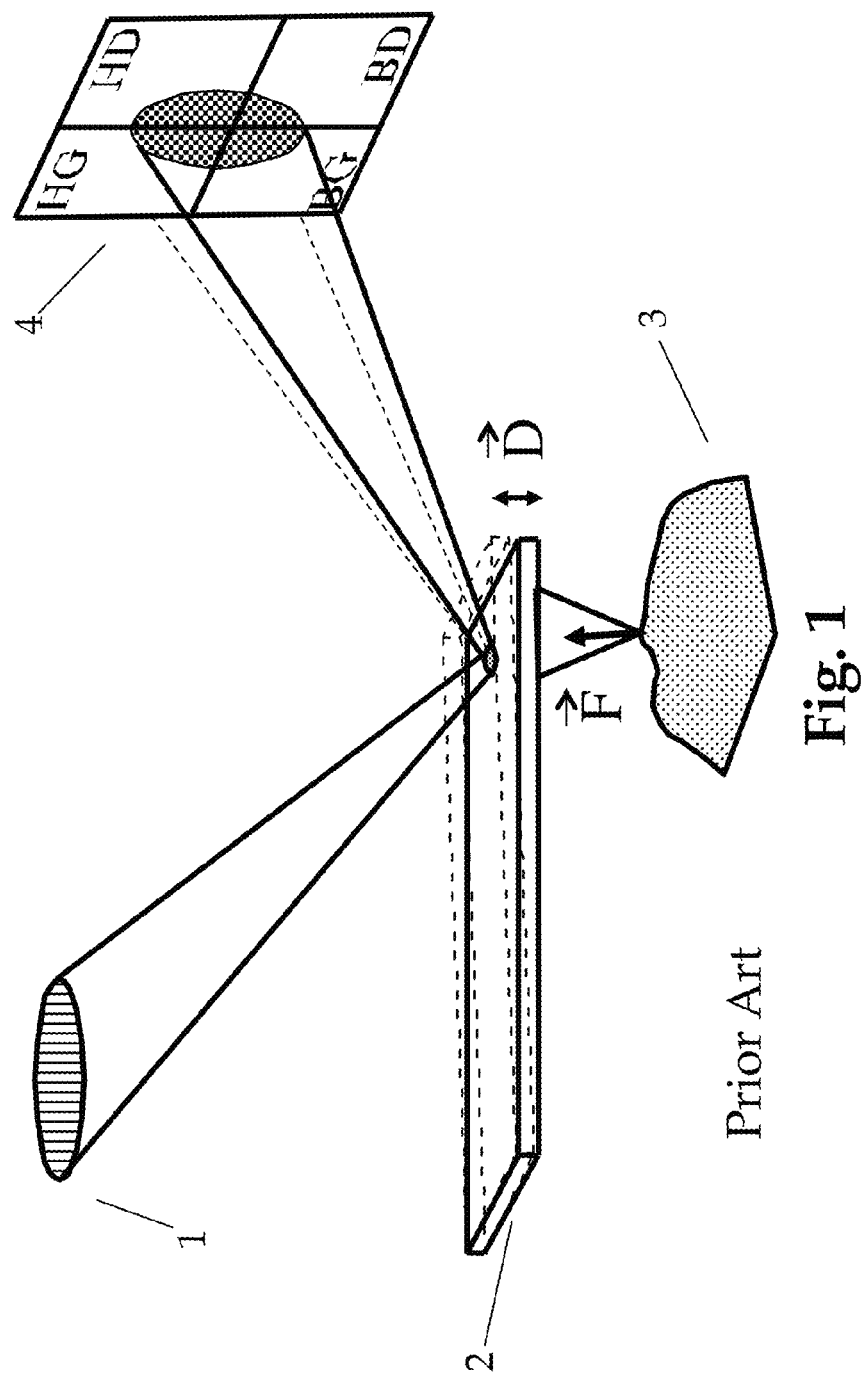
FIG. 1 shows schematically the operation of an AFM.
Figure 2:
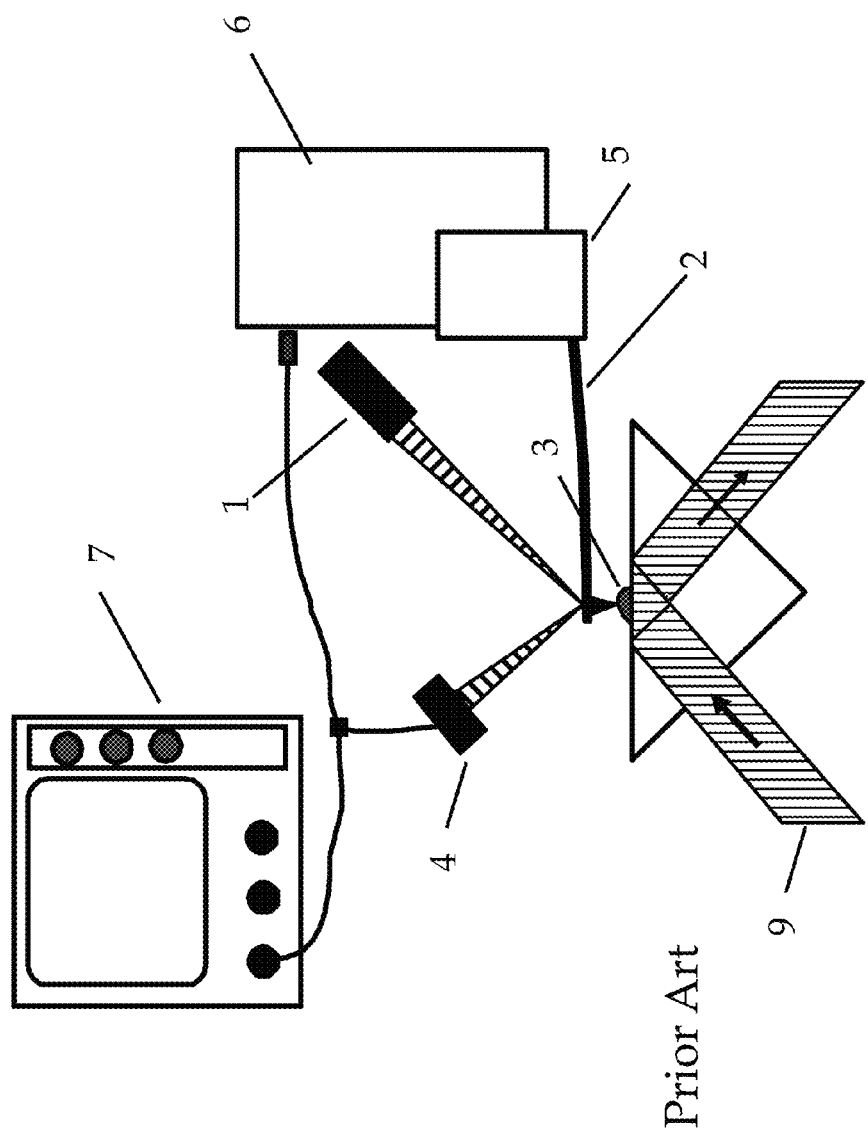
FIG. 2 shows schematically the set-up the prior art version of the PTIR spectroscopy technique.
Figure 3:
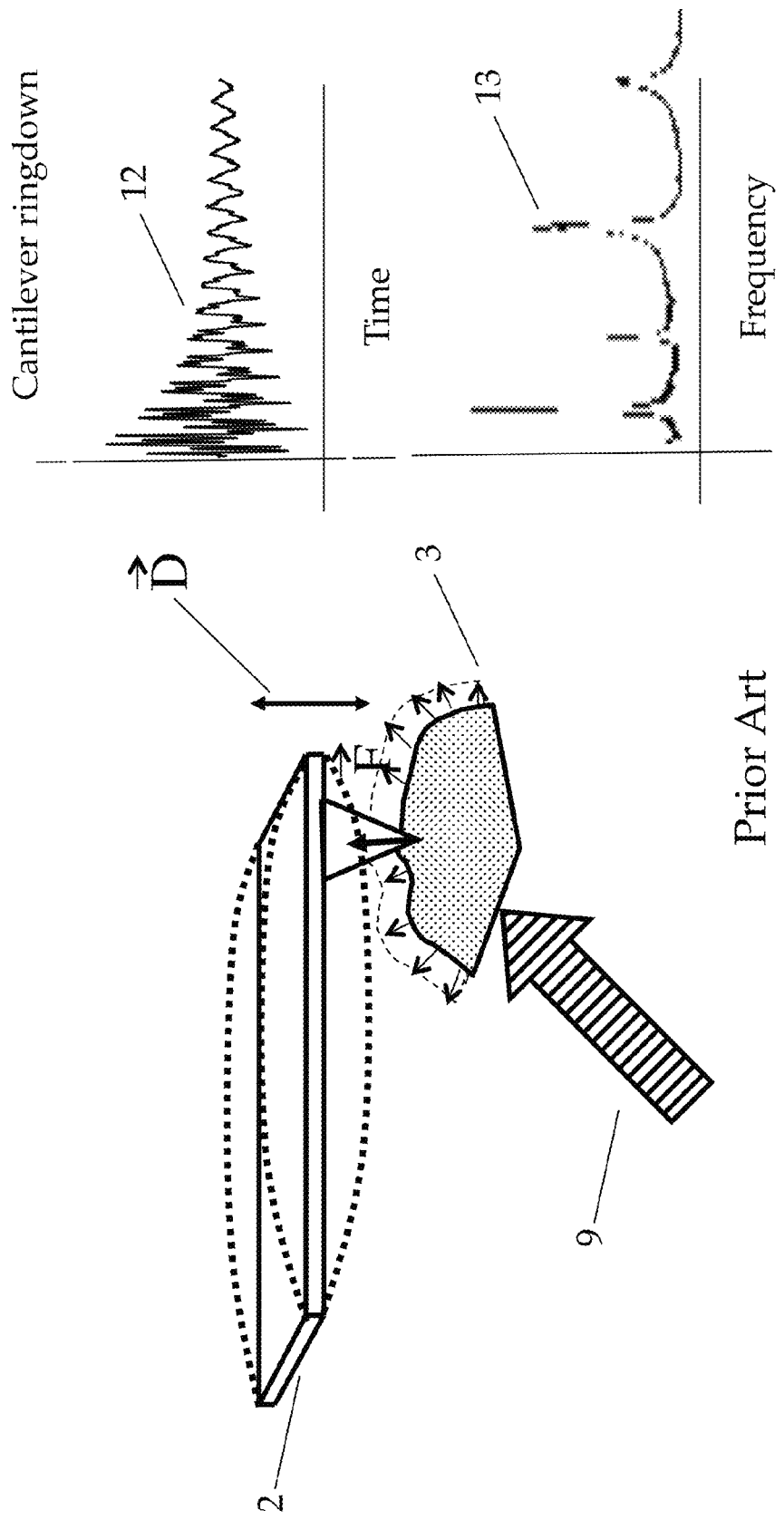
FIG. 3 schematically shows the effect on the cantilever arm when the sample absorbs pulsed IR energy.
Figure 4:
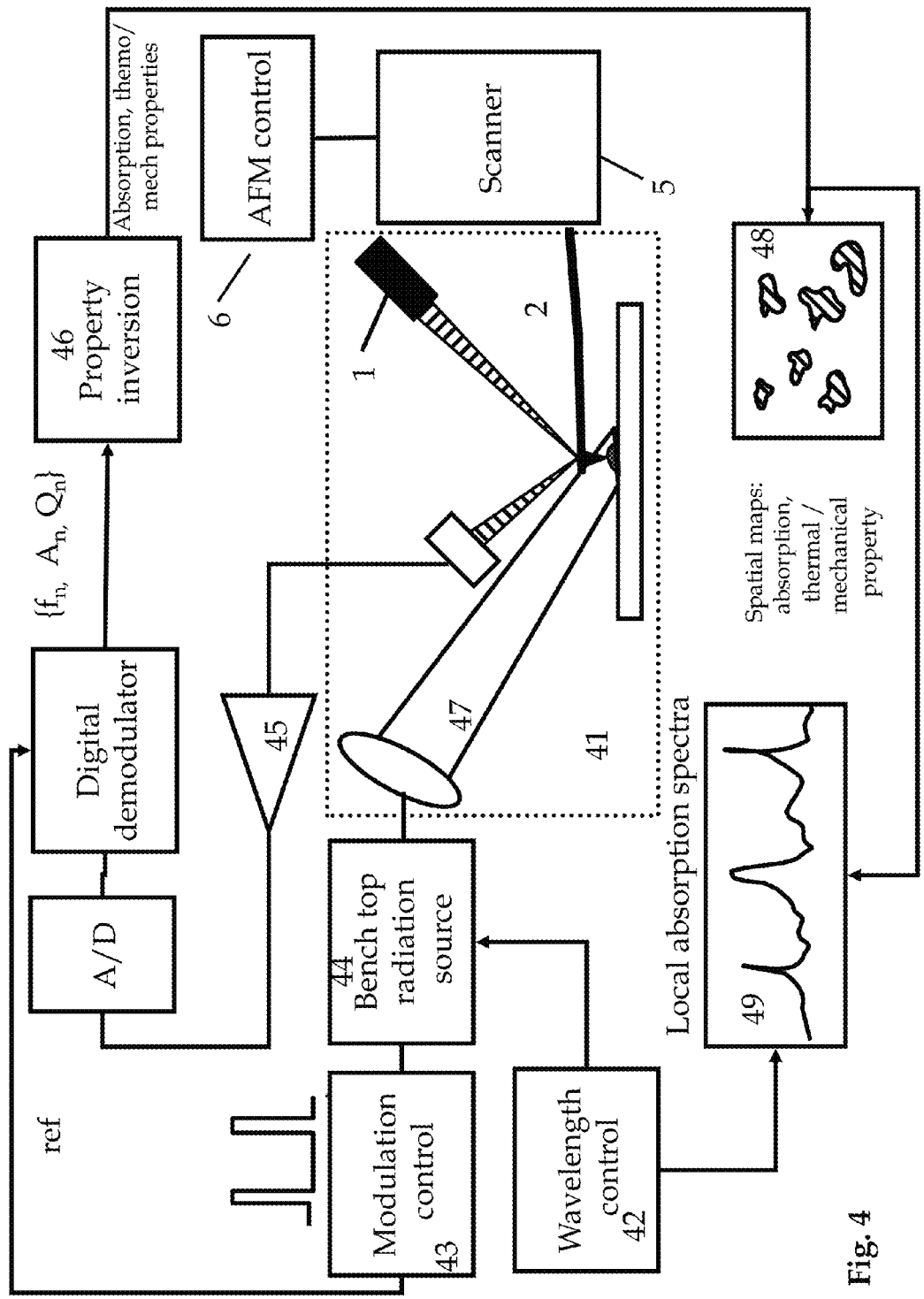
FIG. 4 is a simplified schematic diagram of one embodiment of the PTIR spectroscopy instrument.

Referring to FIG. 3, infrared radiation 9 is incident on a region of a sample 3. At a wavelength absorbed by the sample, the absorption will typically cause a local increase in temperature and a rapid thermal expansion of the sample 3. Probe 2, is arranged to interact with the sample and transducer a signal related to the IR energy in the region under the probe tip. By "interact" we mean to position the probe tip close enough to the sample such that a probe response can be detected in response to absorption of IR radiation. For example the interaction can be contact mode, intermittent contact or non-contact mode. An associated detector can be used to read one or more probe responses to the absorbed radiation. For example the induced probe response may be a probe deflection, a resonant oscillation of the probe, and/or a thermal response of the probe (e.g. temperature change). For probe deflection and/or resonant oscillation of the probe appropriate detectors can comprise split segment photodiodes along with any associated amplification and signal conditioning electronics. In the case of a thermal response, the appropriate detector may comprise for example a Wheatstone bridge, a current and/or voltage amplifier and/or other associated electronics to sense, amplify and condition the thermal signal from the probe. The probe response is then measured as a function of the wavelength of incident radiation to create an absorption spectrum. From such spectra, material in the sample can be characterized and/or identified. The system can also be used to image variations in chemical composition with nanoscale resolution. To enable such measurements, the system is typically set at a fixed wavelength corresponding to an IR absorption band, and then the IR absorption can be mapped as a function of position on the sample. The use of a sharp tip to transduce the local IR radiation absorbed provides the capability to sense and map IR absorption on scales smaller than the diffraction limit. These capabilities are enabled by the combination of several enabling technologies, specifically including elements shown in FIG. 4:

(a) PTIR enabled SPM 41, 42 and 43
(b) Benchtop source of IR radiation 44
(c) IR beam delivery system 47
(d) Cantilever excitation and/or scanning 5
(e) Cantilever motion detection and demodulation 45
(f) Background minimization algorithms 46
(g) Measurement of temperature change
(h) Resolution
(i) Post processing
(j) Spatial maps 48
(k) Local absorption spectra 49

Novel embodiments of these elements will be disclosed in the following sections.

Benchtop Sources of IR Radiation
Optical Parametric Oscillator

In one embodiment, the source of IR radiation is a tunable source of coherent IR radiation. Unlike broadband sources, this source can emit radiation over a fairly narrow wavelength band and then can be tuned to a specific wavelength to create absorption images at a specific wavelength. In one embodiment the benchtop source of coherent radiation is an optical parametric oscillator, OPO, as shown in simplified form FIG. 5 and in more detail in FIG. 6. OPO's convert monochromatic laser radiation (pump) into a tunable output via a three-wave mixing process with quantum conversion efficiencies that can exceed 50%. The heart of an OPO is a nonlinear-optical crystal. In this crystal, the pump photon decays into two less energetic photons (signal and idler) so that the sum of their energies is equal to that of the pump photon. Such instruments are described in detail in the book chapter Pulsed Mid-IR Optical Parametric Oscillators in Solid-State Mid-Infrared Laser Sources, I. T. Sorokina, K. L. Vodopyanov (Eds.) Topics Appl. Phys. 89, 141-178 (2003) Springer-Verlag Berlin Heidelberg 2003.

Figure 5:
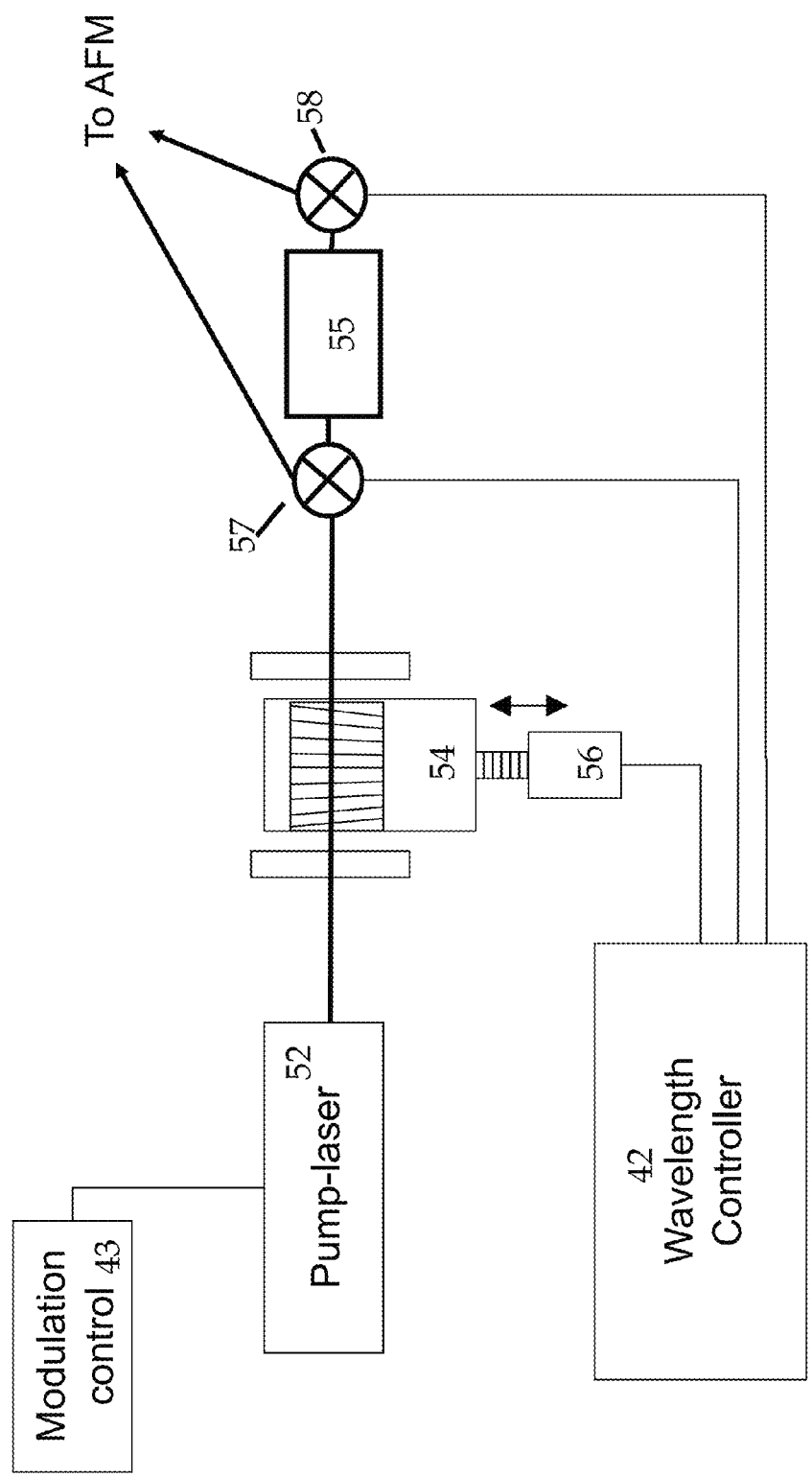
FIG. 5 shows a simplified schematic of one embodiment of a benchtop source of modulated IR radiation using a two stage optical parametric oscillator.

The basic elements of a two stage OPO according to the invention are shown in FIG. 5. The initial radiation source is a pump laser 52. This is generally a lower wavelength, commonly available unit in the one micron or so range. This unit is modulated in frequency and pulse length by modulation source 43, which may be one of several types of optical modulator as will be detailed below. The pump laser is directed into the first stage, an optical cavity 54, consisting of the non-linear crystal and associated optics. Typically the first stage is wavelength tuned mechanically, most commonly by using a crystal with a fan shaped internal structure as shown. The wavelength controller 42 issues commands to a mechanical actuator 56, which displaces the fan perpendicular to the pump beam, thus changing the characteristic cavity length the beam transverses, leading to a change in output wavelength. Thus the wavelength can be tuned over very fine increments at a speed only limited by the actuator.

The output of the first stage is typically boosted up to a range covering several microns, depending on the exact structures used. Thus for the spectral measurements in this range the output is steered by controllable optics 57 directly to the AFM system and sample. Steering optics 57 may consist of a variety of types known in the art, movable mirrors, beam splitters and the like, and may also include filters and focusing elements as needed. For parts of the spectrum requiring higher wavelength illumination, Optics 57 steers first stage output to second stage non-linear crystal 55 instead of directly to AFM. Second stage 55 typically splits photons from the first stage into two new photons of longer wavelengths. In one embodiment, wavelength tuning is still accomplished at the first stage. Second stage output is steered to AFM buy controllable optics 58, which again may be of various types known in the art. Second stage typically boosts first stage wavelength by factors of two to three or more. If required a third or more stages could be added as well.

Figure 6:
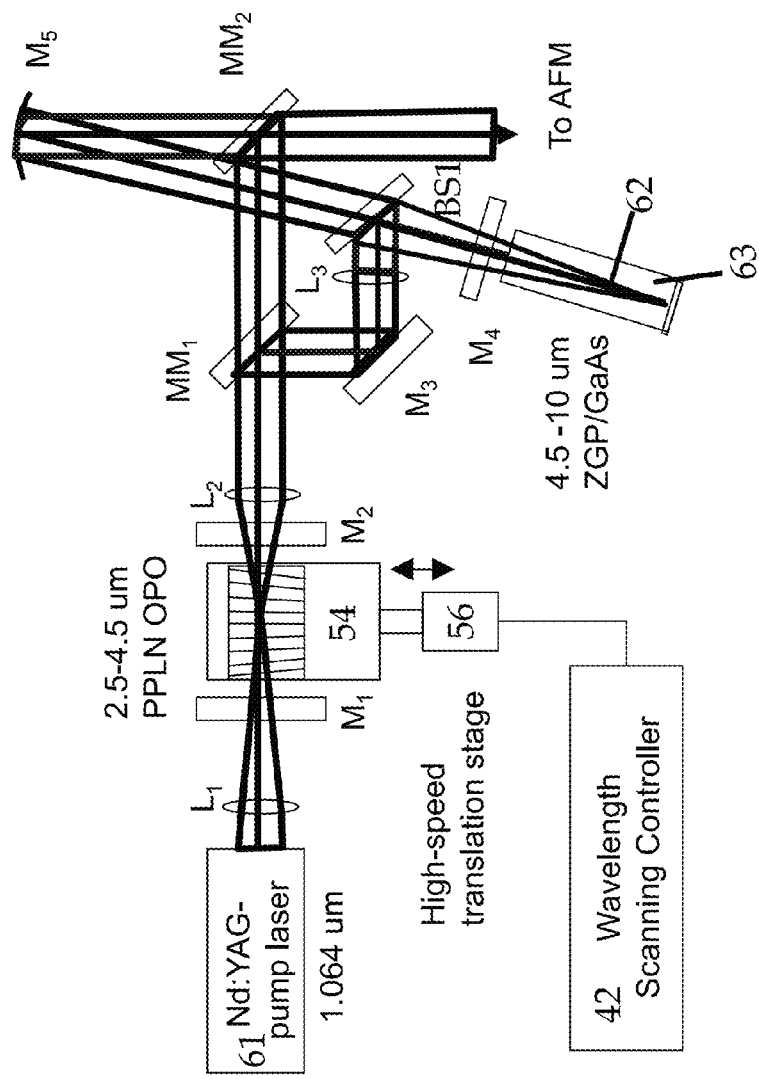
FIG. 6 shows a more detailed schematic diagram of one embodiment of a benchtop source of modulated IR radiation using a two stage optical parametric oscillator.

A more detailed diagram of one embodiment of the IR source is shown in FIG. 6. In this embodiment, the pump laser may comprise a Nd-YAG laser 61 with an output of 1.064 microns. Radiation from the pump laser is focused via lens L1 to a nonlinear crystal 54, which may be periodically poled lithium niobate (PPLN) for example. The PPLN material has a change in its ferroelectric polarity at periodic intervals, corresponding to the coherence length for a desired wavelength. This has the effect of reversing the nonlinear crystal polarity with the right periodicity to allow propagation and hence enhancement of a selected wavelength. As described above, the inventors have employed a PPLN crystal 54 with a "fan" type structure, i.e. where the poling period is varied over the length of the crystal. In this case the crystal can be translated relative to the beam to resonantly enhance a selected wavelength by impinging the pump beam on a region of the PPLN that where the quasi phase matching of the poling period allows transmission of the selected wavelength. Partially reflecting mirrors M1 and M2 form a resonant cavity that in combination with the PPLN crystal can emit radiation covering wavelengths for example from 2.5 to 4.5 um with output power in the range of 10 s to 100 s of microjoules per pulse. Optional lens L2 is used to recollimate the beam from the $1^{st}$ stage OPO such that it can be easily passed to the $2^{nd}$ stage or to the AFM. In one embodiment the inventors have employed a PPLN crystal 54 with a fan pattern stretching over a distance of 25 mm. A motorized actuator 56 under computer control can automatically set and sweep the desired wavelengths. Precision motorized actuators are available for example with top speeds in excess of 1 msec, enabling wavelength scanning to occur on scales as short as tens of milliseconds for a wavelength sweep over two microns or more. Thus in practice, the time required to complete a single IR absorption spectrum may be limited only by the required data acquisition time required to achieve sufficient signal to noise. As shown in FIG. 11b, the inventors have demonstrated the ability to acquire high quality PTIR spectra with data acquisition times of as little as 10 msec per data point. Thus a spectrum with 100 data points obtained at 10 msec per point can be obtained in a little over 1 sec. For a wavelength range of 2800-3600 $cm^{-1}$ this corresponds to a tuning rate of roughly 800 $cm^{-1}$/sec, to our knowledge far in excess of competitive sub-micron IR imaging technologies. For extremely thin films, for example of 100 nm thickness, it can be desirable to use longer integration times, for example 1 second per data point, resulting in a spectra completion time of around 100 seconds. With the same 800 $cm^{-1}$ tuning range, the corresponding tuning rate is around 8 $cm^{-1}$/sec. Note that tuning ranges need not be continuous—it may be desirable to omit regions without absorptions of interest. It can be sufficient to select for example two separate wavelength regions perhaps each 100 $cm^{-1}$ wide and covering absorption regions corresponding to the sample under study.

In one embodiment, the inventors have used PPLN material that is poled with periods ranging from 29.0 to 30.6 um to allow quasi phase matching and hence resonant enhancement for wavelengths 2.3 to 3.7 um. Other fan ranges may also be used.

The inventors have employed a second stage of Zinc Germanium Phosphide, ZnGeP2 (ZGP), which is a highly efficient nonlinear crystal. Using noncritical phase matching, the inventors achieved tuning of the output beam from the ZGP from 3.6 to 10.2 um. Use of a polarizer, for example a wire grid polarizer, can select between the signal and idler beams generated in the ZGP. The ZGP crystal may also be replaced with a GaAs crystal which can provide a tunable second stage range between 4-14 um. Selection between the first and second stage can be achieved using movable mirror MM1 and MM2, for example. When MM1 is in place for example, the output of the $1^{st}$ stage OPO laser is directed off mirror M3, through focusing lens L3, off beamsplitter BS1 and to the $2^{nd}$ nonlinear crystal 62. A resonant cavity is created by the mirror M4 and a reflective surface 63 on the back of the nonlinear crystal 62. The beam exiting the $2^{nd}$ stage is recollimated by mirror M5 before being directed to the AFM. When movable mirror M1 is removed and movable mirror MM2 is inserted into the beam path, the output of the $1^{st}$ stage OPO is sent directly to the AFM. It is generally desirable that the beams from the first stage and $2^{nd}$ stage are substantially collinear such that spectra can be obtained with either stage without requiring time consuming realignment. While one optical arrangement is shown for achieving this, it is understood that many alternative optical arrangements can accomplish substantially the same goal.

Continuous Tuning.

To the inventors' knowledge, the prior art has lacked the ability to rapidly tune over a wide wavelength range with a high repetition rate in a bench top scale instrument. FIG. 5 show an embodiment of a source of IR radiation that is broadly tunable with and can be modulated at pulse repetition rates as high as 5 kHz, while all of the components are small enough to fit within an area of around 2 $m^2$ or less. To enable smooth and fast broad tuning, previously available broadly tunable IR lasers have employed one or combination of temperature tuning and mechanical motion. Temperature tuning requires one or more of the nonlinear crystals to be placed in a temperature controlled oven and the oven temperature is varied to adjust the emission wavelength. Because temperature stabilization can take many minutes, this technique not practical for rapid wavelength scanning as required for spectrum measurements. The current invention avoids the need for temperature tuning and hence enables much more rapid acquisition of material spectra. Using computer controlled motorized wavelength scanning it is possible obtain AFM based absorption spectra over a range of >1000 $cm^{-1}$ in less than one minute and in fact in times shorter than a second. This corresponds to a tuning rate in the range of 16 to over 1000 $cm^{-1}$/sec. For example, the first stage of the OPO laser can cover frequencies from 2800 to 4000 $cm^{-1}$ with tuning of the first stage only.

Source Modulation

The IR source is typically modulated to induce a dynamic response of the cantilever. The modulation may be sinusoidal, square wave, pulsed or other periodic modulation patterns. In one embodiment, employing an OPO the IR source was pulsed by pulsing of the Q-switched YAG nanosecond pump laser. The inventors have used pulses in the range of 10-30 nsec, but longer and shorter pulses can also be suitable. As opposed to commercially available picosecond OPO lasers with typical pulse repetition rates in the range of tens of Hz, the inventors have also employed pulse repetition rates as high as 5 kHz. Suitable pump lasers for OPO crystals can operate at many tens of kHz. The larger repetition rate of our nanosecond OPO source allows generation of hundreds or thousands more IR pulses per second. This allows the probe signal from many more pulses to be averaged in the same amount of time, enabling significantly better signal to noise ration and/or improved measurement speed. The source can also be modulated using mechanical choppers, acousto-optic modulators and/or other devices that provide a periodic variation in the optical output. The modulation can be pulses, sine waves, square waves or more complex periodic waveforms including stochastic modulations. Note that the modulation need not be internal to the IR source, but may instead be located externally as long as the modulation occurs before the radiation is incident on the sample.

Laser Power and Spectral Resolution

Using a 30 nsec pulse laser, the OPO is capable of delivering pulses of roughly 50-300 uJ in the first stage between 2.5-4.5 um. For 4.5-8 um, it can deliver 10 uJ and 1 uJ from 8-10 um. The spectral linewidth of the source is typically less than 32 $cm^{-1}$ and in many regions <8 $cm^{-1}$, thus providing resolution sufficient to match typical IR materials databases.

Alternative: Quantum Cascade Laser (QCL) Array

Alternative benchtop sources with acceptable characteristics may be possible. Individual Quantum Cascade Lasers are currently narrowly tunable, but can be assembled into an array that is tunable over specific wavelengths of interest. For example, QCLs from Daylight Solutions, for example are available with center wavelengths including 4.9, 5.2, 6.1, 7.7, 8.8, 9.2, 9.7 and 10.5 um. Each laser may be rapidly tuned by 100 cm-1 and an array of such QCLs can be integrated to provide broad coverage of wavelengths of interest in the mid-IR. QCLs have the advantage that they can be pulsed at much higher frequencies than OPO sources, up to roughly 100 kHz, thus providing the capability for direct synchronous modulation of the cantilever resonance for some cantilevers, i.e. with one pulse per cantilever resonance cycle. Or for higher order modes, the QCLs are fast enough to provide pulses every few cycles versus every few hundred cycles.

Bench Top Footprint

Either the OPO, as described above, or the QCL devices are small enough to be packaged as a benchtop device. Note that by use of the term "benchtop" we are referring to systems generally small enough to fit on a typical laboratory bench. This means a footprint of less than roughly 1 m high, 2 m long and 1 m deep. It does not imply that the benchtop source of IR radiation actually sit on a bench. It may instead be located on the floor or installed in an electronics rack. The term "benchtop source of radiation" is intended to distinguish the invention from other sources that are either entire facilities (like the FEL) or other large sources that may be as large as a room.

Beam Delivery Systems

Figure 7:
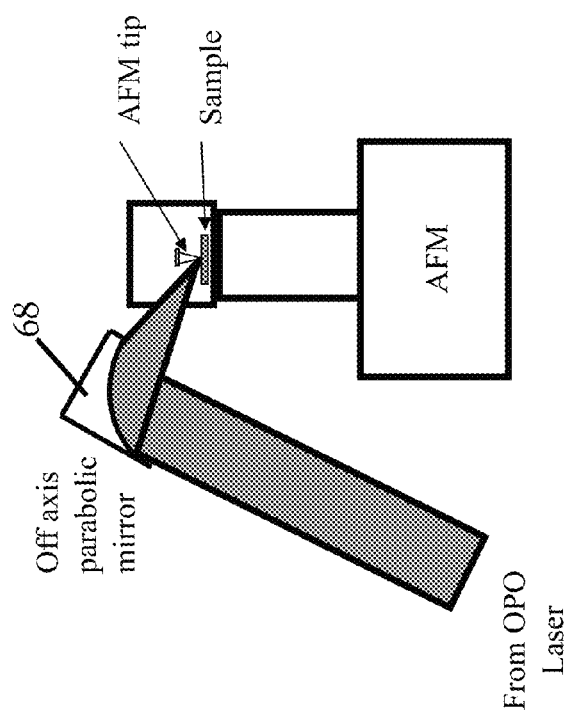
FIG. 7 shows a simplified schematic diagram of a beam delivery system for supporting top down illumination on a commercial scanned sample AFM.
Figure 8:
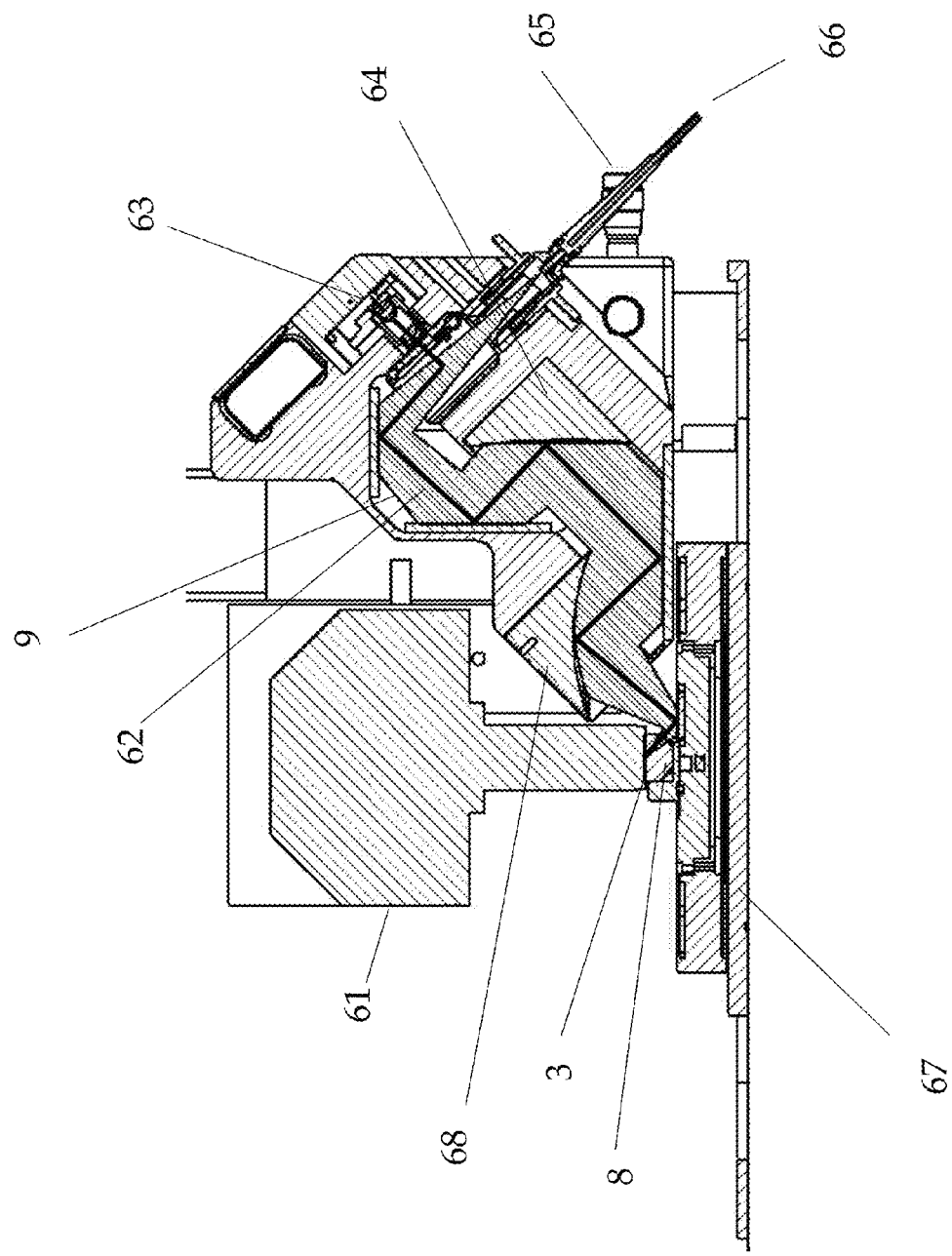
FIG. 8 shows a simplified schematic diagram of a beam delivery system for supporting top down illumination for another commercial AFM.

The job of the beam delivery system is to optically couple radiation from the benchtop source of IR radiation to a region of the sample where it can be sensed by the cantilever. The radiation may be optically coupled to the sample through a free space beam, through evanescent coupling, and/or directed by one or more optical elements in the beam delivery system. The beam delivery system may comprise lenses, mirrors, prisms, optical fibers and/or other components to transmit and focus the beam from the source onto the desired region of the sample. The beam delivery system typically has optomechanical adjustments to allow the beam to be aligned with a region of the sample under the probe tip. A drawback with the prior art laboratory set-up is the need to mount the sample on a prism. Samples for bottoms up illumination often need to be less than 1 um in thickness. In practices this includes samples that can be vacuum deposited, deposited from solution, dip coated, spin coated, and/or microtomed onto the prism. Some samples, for example pharmaceutical samples, membrane samples, coatings on specialized substrates and friable materials are less amenable to this type of sample preparation. For such samples it is desirable to provide top-down illumination and the ability to measured native, unmodified surfaces. Thus a beam delivery system takes the beam from the benchtop IR source and directs it onto a desired region of the sample from above is desirable. An example embodiment of such beam delivery system is shown in FIGS. 7 and 8. In one embodiment the beam delivery system further has the ability to focus the IR laser beam 9 to a spot and adjust the relative position of the spot on the sample. The inventors have developed a beam delivery system that is compatible with both the prior art technique of placing a sample on an IR transmissive prism 8 or the newly developed technique of top down illumination for samples difficult or impossible to mount on a prism.

Laser Focus

To facilitate optimal IR signal strength it is often desirable to focus the incoming light beam to a tightly focused spot. For focus systems using lenses, suitable lens materials may include CaF2, BaF2, ZnSe, germanium and silicon lens elements for example. Multiple mirrors and/or lenses may be used to achieve better focus, for example by expanding the beam before the final focus lens or mirror. Multiple optical elements may also be used to balance spherical and/or dispersive aberrations.

In one embodiment as shown in FIG. 7, the incoming light is focused by reflective optics, for example a parabolic reflector 68. The parabolic reflector has the advantage of focusing at the same position for all wavelengths. The arrangement is FIG. 7 is suitable for example for directing and focusing IR radiation to the sample of some commercially available AFMs, for example the MultiMode AFM manufactured by Veeco Instruments. In this embodiment, the beam is focused through an opening in the front of the AFM head and impinges on the top surface of the sample. FIG. 11a shows an example PTIR absorption spectrum taken using this embodiment using an off axis parabolic mirror with a 50 mm effective focal length and an optical parametric oscillator as the IR source.

In another embodiment, as shown in FIG. 8, radiation 9 from a benchtop IR source is brought to the vicinity of an AFM 61 using a mid-IR transmissive fiber 66. Suitable fibers are made for example from silver halide and chalcogenide materials and are available from several vendors. In one embodiment, the inventors have employed a silver halide fiber with a core diameter of 200 um.

Light exiting the fiber is collimated using a first off axis parabolic (OAP) reflector 64. The collimated beam is then directed off optional turning mirrors before being focused with a second OAP 68. The pair of OAPs serve to demagnify the size of the IR light spot when delivered to a sample. In one embodiment the inventors have arranged OAPs with focal lengths and distances to provide a 3× reduction in spot size, for example imaging the light emitted from a 200 um core of the fiber to a final spot size of around 67 um. This arrangement can be useful for interfacing the PTIR technique to other commercially available AFMs, including tip scanning AFMs like the Dimension AFM system available from Veeco Instruments.

To accommodate variations in sample height and to achieve optimal sensitivity it is also desirable to also include a focus axis adjustment such that the probe and sample are near the optimal focus position of the focusing optics. Suitable focus adjustments may comprise mechanical translation stages, focus rings, flexures piezoelectric actuators and/or similar precision actuators. The range of motion is generally chosen to coincide with variation in sample height to be accommodated, and the precision is generally determined by the depth of focus of the IR optics.

Laser Alignment

It is generally desirable to align the focused laser spot onto an area of the sample in close proximity or overlapping with the probe tip. This alignment generally provides higher sensitivity to the thermal expansion of an absorbing region directly under the AFM tip. Such an alignment thus can provide better immunity from background absorption of neighboring regions of the sample.

This alignment can be tricky, however, because the infrared beam is not visible to the human eye. The IR laser beam can be viewed by specialized IR cameras and alignment can be achieved by viewing the position of the IR beam in the display of such a camera. Alternately, it is possible to integrate a visible guide beam, for example from a HeNe laser or visible laser diode 63. By careful design, assembly and/or alignment 65, the visible laser can be made collinear with the IR beam.

In a preferred embodiment it can also be made parfocal. One means of achieving this alignment is to shine the focused IR beam 9 onto a piece of metal, especially a piece of metal coated with graphite. When the metal/graphite absorb IR radiation with sufficient intensity, a local plasma is created and this plasma can be viewed visually. Then it is possible to align the visible laser beam with the glowing plasma. A related technique to achieve alignment with the visible guide beam is to focus the IR spot on a material with sufficient IR absorption to locally melt. The local melted region can be viewed in an optical microscope and the guide beam aligned to the melted spot. It is generally desirable, but not required, that the guide beam alignment be performed at the factory to facility easy alignment of the IR beam by a user.

Once the visible guide beam 62 is aligned with the IR beam 9, the IR beam 9 can be simply aligned by viewing the position of the visible guide beam in an optical microscope. The IR beam is steered to the desired location relative to the probe and sample using a beam steering mechanism, for example a kinematic tilt stage, an XY translation stage, piezo stage or other actuator capable of moving the beam position relative to the cantilever probe. As a guide to the user, it can be desirable to provide crosshairs in an optical microscope or video screen to identify the optimal alignment position.

In the previous discussion it should be made clear that suitable alignment can be achieved by moving the probe, the IR beam or a combination of both.

In addition to using the visible laser beam, it is often desirable to perform a final alignment using the strength of the cantilever response as an indicator of desired alignment. The inventors have also used the strength of individual peaks in the Fourier transform of the cantilever motion to determine the optimal alignment. For example, in some cases, it may be desirable to align the IR laser spot such that the position substantially maximizes a higher mode of the cantilevers oscillation. As discussed elsewhere, the inventors have found that in some cases the cantilever's fundamental response may be heavily influenced by non-local forces away from the cantilever tip. In this case, optimization of laser alignment that substantially maximizes the amplitude of the $2^{nd}$ mode, for example, can provide a higher quality spectrum with less background influence.

It is also possible to include automated laser alignment by employing electronic actuators that drive the IR laser spot to a desired alignment, based on any of the techniques mentioned above. Suitable electronic actuators are made by New Focus and Newport, for example.

Other Beam Delivery Systems for Top Down Illumination

Figure 9:
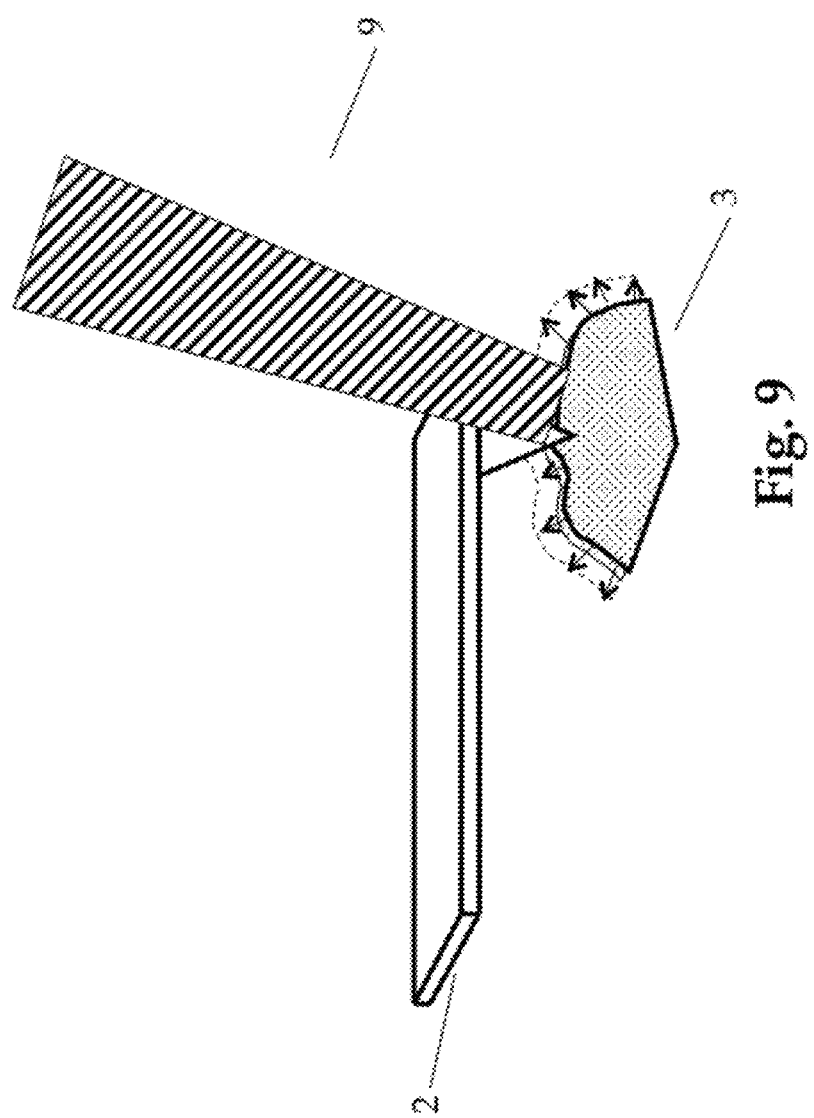
FIG. 9 schematically shows the case where the sample is illuminated from above the plane of the sample with a transparent cantilever.
Figure 10:
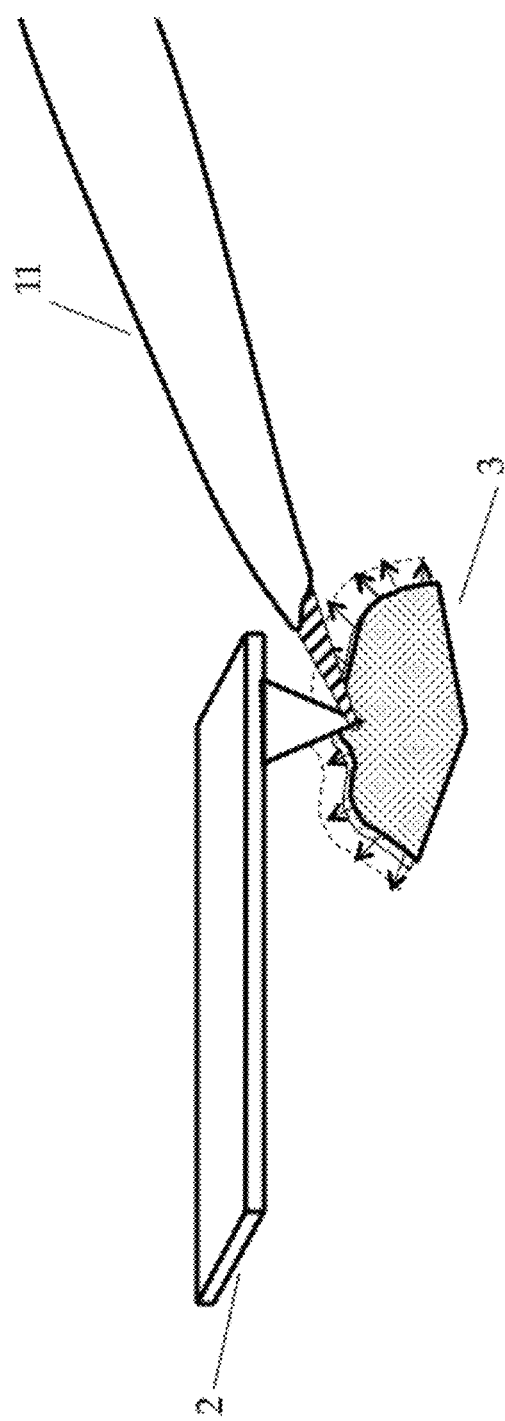
FIG. 10 shows a simplified schematic diagram of an alternative beam delivery system for supporting top down illumination.

One alternative, which can greatly simplify the beam steering system is to us a transparent cantilever, as shown in FIG. 9. Other advantages of an IR transparent cantilever will be discussed below. Another alternative approach for top down illumination is to employ an optical fiber or other waveguide 11 as the IR beam delivery system as shown in FIG. 10. If the fiber or waveguide 11 is placed close enough to the sample surface, focusing optics may not be necessary. It is also possible to incorporate a focusing element onto the end of a fiber, for example a Fresnel lens. The use of top down illumination enables almost unlimited range of samples and makes it possible to make full use of the capabilities of most AFMs without putting constraints on the method of mounting the sample.

Cantilever Excitation

Figure 17A:
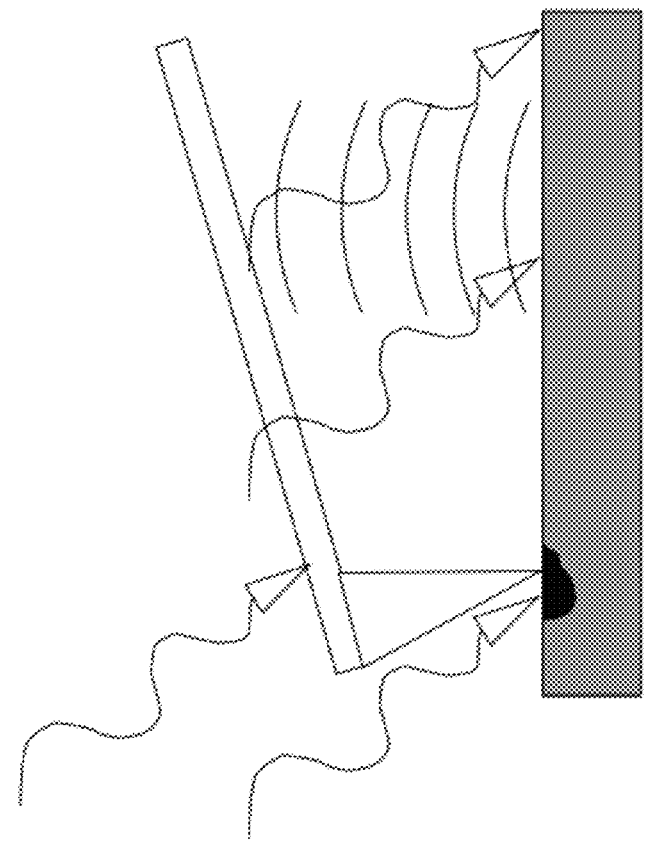
FIG. 17a shows schematically some sources of potential background signal that may be detected by the AFM cantilever.
Figure 17B:
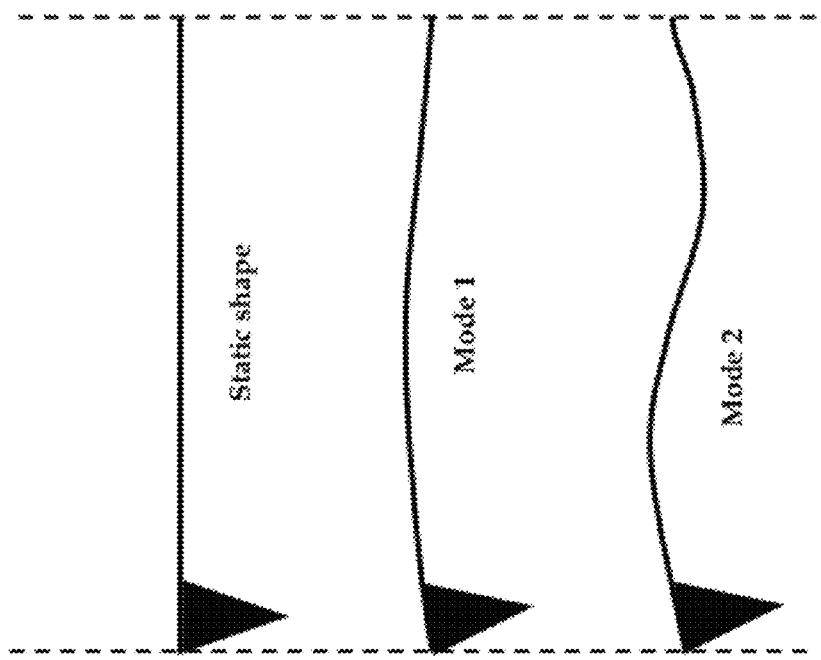
FIG. 17b shows the approximate static shape of the cantilever and the first two mode shapes of flexural vibration.

The cantilever probe is brought into interaction with the sample. The interaction can be contact, intermittent contact, and/or non-contact. Absorption of radiation by the sample is used to excite a detectable response in the probe. In one embodiment, the rapid thermal expansion of the sample can induce resonant motion of the probe. In the case of contact mode AFM operation, the tip is generally in continuous contact with the sample. Rapid thermal expansion of the sample induces a shock pulse that typically excites multiple resonant modes of the cantilever probe. These resonant modes are called "contact resonances" in the literature and roughly correspond to analytical predictions for beams that are fixed on one end and pinned on the other. An example of the mode shapes for the first two modes of a typical cantilever are shown in FIG. 17*b*. In general modulation of radiation from the benchtop source of IR radiation will induce some combination of static deflection and/or ac oscillation or a more complicated transient response. Any of these induced motions can be used as the probe signal and be representative of IR absorption by the sample.

For widely separated IR pulses, the resulting cantilever motion will often be a series of decaying oscillations of one or more excited modes of the cantilever. An example decay curve 12 is shown in FIG. 3. This decaying oscillatory motion is the sum of motion of each of the individual contact resonances excited by the IR pulse. These frequencies may correspond to vertical, lateral, torsional and/or other more complicated modes. Some of these contact resonant modes are described in various papers, for example by Olaf Walter and colleagues, in Ultrasonics 40 (2002) 49-54. The exact frequencies at which these modes occur depend on mechanical properties of the cantilever, the sample and the tip-sample interaction.

Some of these modes are also preferentially excited by the background forces that act over a wider area of the cantilever. In following sections we will describe how to reject background forces to enhance sensitivity to forces at the probe tip.

In one embodiment, the probe is oscillated in and out of contact with the sample, a technique generally referred to as TappingMode or intermittent contact mode. In this mode, the probe may be used to simultaneously or sequentially collect images of the phase of the cantilever oscillation, as described in U.S. RE36,488. These phase images can provide qualitative images of the distribution of material on a sample in aid of nanoscale IR measurements described in this application.

Various parameters can be extracted from the cantilever motion. The resonant frequencies of the contact resonances can give information about the mechanical properties of the probe and sample. The decay times are related to the viscoelastic properties of the sample material (along with other damping forces). The peak amplitude is related to the amount of IR absorption, along with the thermal properties, including thermomechanical properties, of the sample, these include heat capacity, thermal conductivity and coefficient of thermal expansion. The section below on Signal Conditioning and Analysis will describe techniques for separating these effects to extract specific parameters of interest which then permit localized measurements of IR spectra and spatial maps of IR absorption.

Alternately, the IR source can be modulated or pulsed in synchronization with the cantilever motion to build up a steady state oscillation amplitude. Note that it is not necessary to have one pulse for every oscillation cycle. Instead the IR source can be arranged to pulse every N cycles of the cantilever oscillation. For example a cantilever with a mode resonance of 300 kHz can be excited with a pulse repetition rate of 1 kHz as long as the pulses maintain a substantially constant phase with the cantilever oscillation, i.e. one pulse every three hundred cantilever oscillation cycles. Maintaining the appropriate phase arrangement ensures that a steady state amplitude is generated.

Cantilever Demodulation

In this context, cantilever demodulation refers to techniques to extract and isolate the cantilever's response to the radiation absorbed by the sample. The relevant cantilever response can be vertical deflection, lateral deflection, thermal response (e.g. temperature increase) or a combination of these.

Cantilever Oscillation and Ringdown

When the cantilever is periodically excited by the rapid thermal expansion of the cantilever, dynamic response consists of the excitation and then decay of various cantilever oscillation modes. As mentioned earlier, some of these modes are more or less sensitive to the IR absorption right under the tip and others are more sensitive to background forces. For this reason, it is sometimes desirable to demodulate the cantilever deflection into specific frequency components or Fourier components. This can be done in several different ways. First, the cantilever's' time varying deflection signal can be Fourier transformed, for example, by an FFT algorithm. A typical cantilever ringdown 12 and an FFT 13 of this signal is shown in FIG. 3. From the FFT, specific frequency bands can be analyzed, as will be discussed below in the Analysis section.

It is further possible to use a lock-in amplifier and/or RMS detector. Such detectors can be implemented in analog and/or digital electronics to measure the amplitude and/or phases at desired frequencies. The lock-in technique is especially desirable in the case that the cantilever is excited synchronously with the cantilever resonance. In this case, a steady state oscillation will develop and can be easily demodulated with phase sensitive detection. Multiple lock-ins and/or the lock-in reference can be changed to detect oscillatory motion at multiple frequencies. In the case of RMS detection, high and/or low pass filters can be arranged before the RMS detector to select a particular frequency band. RMS detection has the advantage that it can be generated or computed very quickly enabling high data rates.

The hardware and software described below in the Data Collection and Signal Conditioning sections can be operated to generate signals at very high rates. As such it is possible to obtain spectra covering at least 800 $cm^{-1}$ of spectral range with a resolution of better than 32 $cm^{-1}$ in less than 1 minute. It is further possible to obtain a spatial map of IR absorption with a resolution exceeding 100×100 pixels in less than fifteen minutes.

Probes for PTIR

A wide range of AFM probes provide good PTIR results. The inventors have employed cantilevers made from silicon, silicon nitride, silicon dioxide and other materials, with and/without reflective coatings, and with spring constants range from 0.001 N/m to 10 N/m and with resonant frequencies from ten kHz to several hundred kHz. The inventors have also employed cantilevers that may be self heating and/or temperature sensing, for example the ThermaLever™ probes available from the assignee. For these reasons, it is often acceptable to choose a suitable probe on the basis of other experimental parameters, for example the tip sharpness or spring constant required to image a sample successfully by conventional AFM techniques.

It is worth mentioning some parameters that can favor PTIR measurements.

(2) Low IR absorption. It is generally desirable to use materials with a low IR absorption coefficient over the region of spectral interest for a sample under study. This can be achieved using cantilevers that are either highly reflective to IR radiation or highly transmissive. The inventors have employed both totally uncoated silicon cantilevers which are generally transmissive in the mid-IR and gold coated silicon and silicon nitride cantilevers, which are reflective. Both types of levers can provide acceptable results. A gold coating of greater than 15 nm, for example may be sufficient to reflect more than 96% of the incident IR radiation.

(3) Low bimetallic bending. It is often desirable to use probes that have minimal bimetallic bending such that any radiation absorbed by the cantilever does not induce excessive parasitic bending of the cantilever that could be confused with sample IR absorption. This guides towards a cantilevers with a reflective coating that is thin enough relative to the cantilever material to permit minimal bending. Alternatively, the cantilever can be coated on both sides to balance the bimetallic bending effect. Solid metal cantilevers can also be used, thus eliminating bimetallic bending due to dissimilar materials. (There can still be cantilever bending due to temperature gradients in the cantilever.)

(4) Cantilevers with minimal surface area exposed to the sample. As the surface area facing the cantilever can receive a thermomechanical shock that induces oscillation, it can be desirable to minimize this surface area. Larger tip heights, for example greater than 1 micron and preferably greater than 10 um, can also reduce this effect also.

(5) High optical lever sensitivity. These levers produce a larger change in cantilever angle for a given vertical deflection. This requirement generally favors shorter cantilevers, but this must be balanced against the spring constant and the imaging force that can be sustained by the sample.

(6) Spring constants. Lower spring constants will produce a larger instantaneous deflection. Short but thin cantilevers can combine a low spring constant and a high optical sensitivity.

(7) Sharp tips. Cantilever probes with sub-micron tip radii can provide superior spatial resolution. Many commercially available AFM probes have a tip end radius smaller than 50 nm.

(8) Tip location. It is often desirable to have the tip at the extreme end of the cantilever. This allows for easier placement of the tip on a desired region of the sample. It also reduces problems of background absorption of the cantilever by allowing minimal overlap between the IR spot and the cantilever body. This also makes the illumination pattern more uniform with less scattering and shadowing.

In alternate embodiments, the probes may be needle type probes akin to those used in scanning tunneling microscopy or membrane probes, like the FIRAT technique developed by Levent Degertekin at Georgia Tech.

Data Collection and Synchronous Averaging

There are many acceptable ways to collect and process the data from the cantilever deflection. The inventors have used a digital oscilloscope, for example to sample roughly 10,000 data points in each cantilever ringdown event. As described below, it can be advantageous to set the acquisition window large enough to cover two or more ring down events. We generally average multiple cycles of cantilever ringdowns to improve the signal-to-noise ration for the acquired data. We employ a sync signal from the pulsed laser to trigger the data acquisition and synchronous averaging using a using a standard feature on a WaveRunner 6050 Oscilloscope from LeCroy, for example. The inventors generally average 2 two to several thousand cantilever ringdowns for each data point in a spectrum or image.

Figure 12:
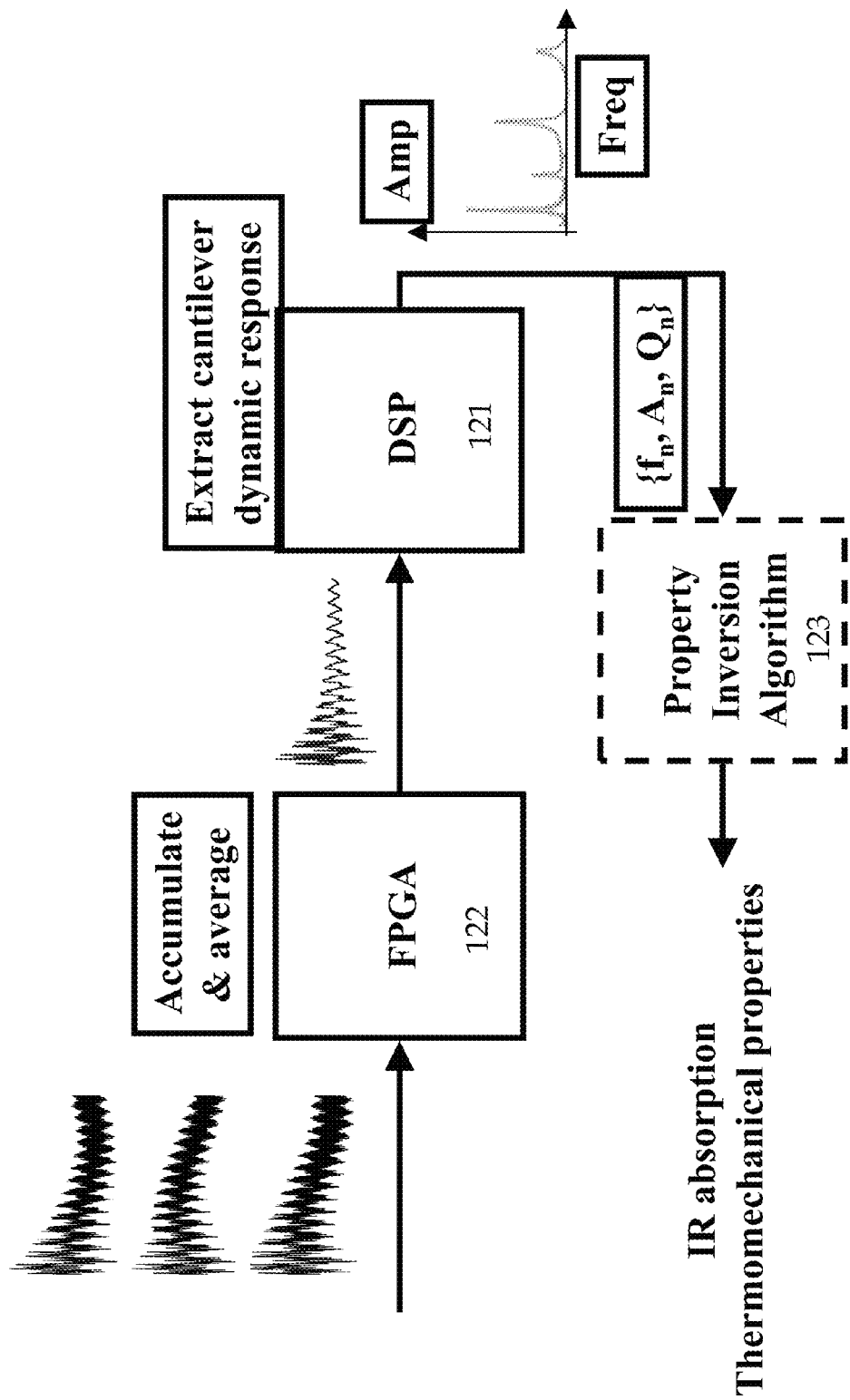
FIG. 12 is a simplified block diagram of a data acquisition and control system capable of measuring and conditioning signals from nanoscale IR absorption measured by an AFM cantilever.
Figure 13:
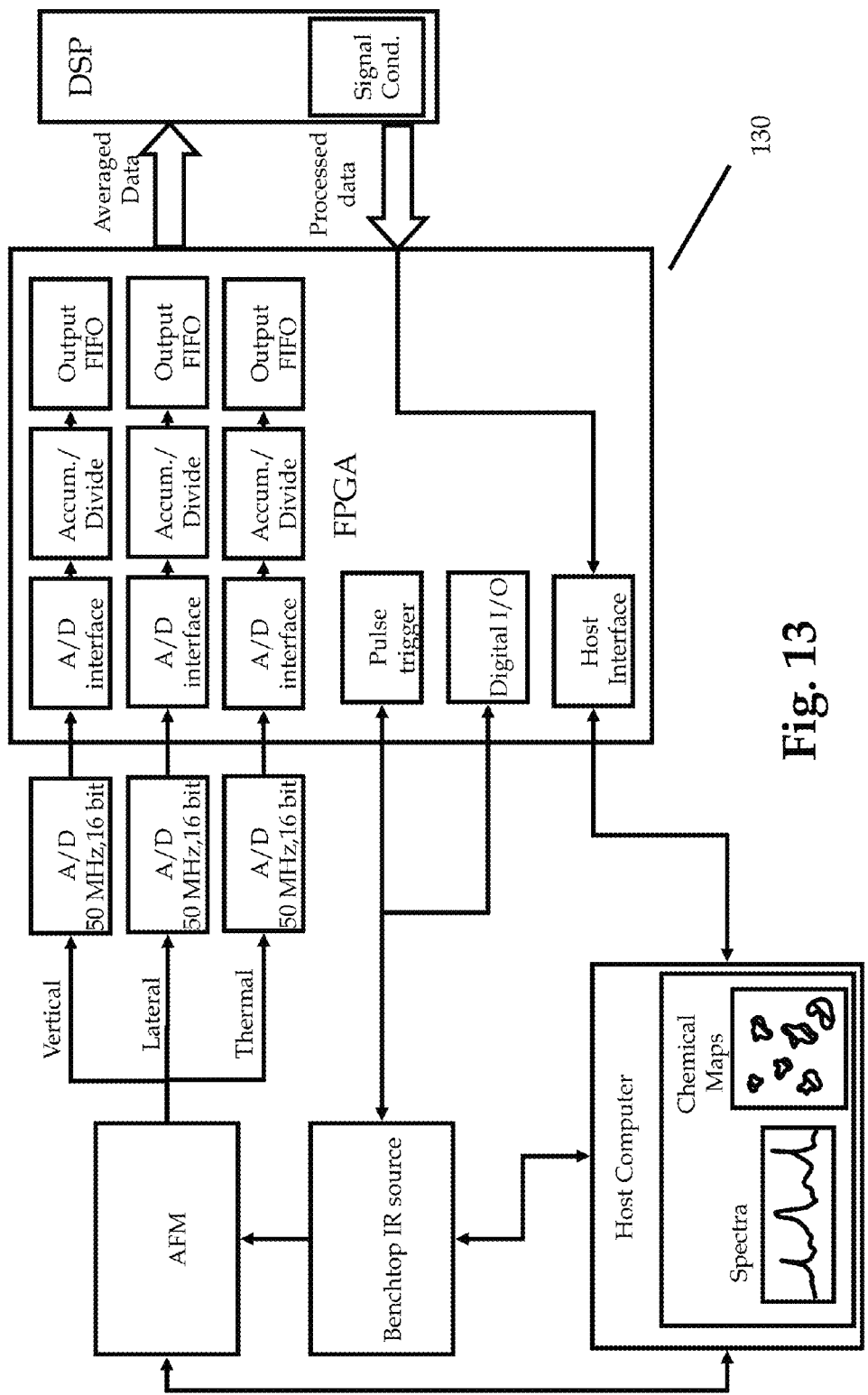
FIG. 13 is a more detailed block diagram of a data acquisition and control system capable of measuring and conditioning signals from nanoscale IR absorption measured by an AFM cantilever

Dedicated data acquisition and control systems may also be employed. For example, high speed data acquisition and processing systems can be constructed from readily available analog-to-digital converters (ADCs), digital signal processors (DSPs) and/or field programmable gate arrays (FPGAs). A schematic diagram of one suitable data acquisition and control system is shown in FIG. 12 and in more detail, 130, in FIG. 13. In one embodiment, ADCs sample the cantilever motion at up to 50 MHz. A pulse trigger from the FPGA 122 initiates a laser pulse from the benchtop IR source. Data acquisition events are generally synchronized to the pulse trigger so that the response from each pulse may be synchronously averaged. Note it is also possible to trigger the FPGA 122 using an external trigger provided for example by the IR laser. The use of the same source (e.g. the FPGA) to trigger both the laser and the data acquisition reduces jitter in the data acquisition. It can also be beneficial to make the laser pulses and the data acquisition triggers synchronous to the phase of the cantilever oscillation, especially in cases of driving the cantilever to a steady state oscillation condition.

The cantilever response to a series of pulses are loaded into the FPGA 122 and synchronously averaged using the Accumulate/Divide blocks. For the most rapid data rate one can limit the number of averages to a power of two, e.g. 64, 128, 256 etc. This allows the FPGA to efficiently create the averaged waveforms by accumulating each waveform into a buffer and then using a binary shift operation to divide by the number of samples to create the averaged waveform.

The output of the FPGA 122 represents the dynamic response of the cantilever to the IR energy absorbed by the sample. This data is typically sent to a Digital Signal Processor (DSP) 121 and/or host computer for further signal conditioning and post processing. This later processing can also be performed in the FPGA alone. The system shown in FIG. 12 and FIG. 13 can support the simultaneous dynamic measurement of vertical and lateral deflection as well as transient thermal response. (Other channels can be added by adding more ADC channels). These signals can be manipulated in a variety of ways to generate absorption spectra of samples and/or spatial maps of IR absorption.

Digital communication between the FPGA 122 and/or host computer and the IR source is used to control parameters of the IR source, including output power, pulse repetition rate, wavelength, and/or wavelength scanning paramters. Additional interfaces (not shown) can be used to monitor the laser power to be used for normalization of the cantilever response as a function of time or wavelength.

Data is typically collected and analyzed in one of two modes. In the "point spectrum" mode, the AFM probe is maintained at a substantially fixed location while the IR source is swept over a range of wavelengths. The cantilever motion is then analyzed to construct a signal representative of the IR absorption as a function of wavelength. (Note that it is common in spectroscopy to plot absorption as a function of wave number, which is the inverse of wavelength. When we refer to a signal versus wavelength, it should be understood that the data can equivalently be plotted versus wavelength or versus wave number).

Alternatively, in the "absorption mapping" mode, the IR illumination can be fixed at a specific wavelength and the probe is scanned relative to the sample surface. In the absorption mapping mode, the IR wavelength is usually set to a characteristic absorption of one of the components of the sample. Thus the distribution of the component can be mapped spatially as a result of the intensity of IR radiation absorbed at the characteristic wavelength, as illustrated by the spatial map 48 in FIG. 4. For absorption mapping mode it is generally desirable to have data collection and analysis algorithms that are very fast such that the absorption at each pixel can be measured as quickly as possible. The data acquisition and analysis hardware described herein can produce an IR absorption signal in ranging from 10 msec-360 msec per pixel. These rates are enabled by the combination of the high pulse repetition rate of the benchtop source of coherent IR radiation and additionally the high data acquisition and averaging rate of the data acquisition and signal condition electronics described above. Together these systems allow a 100× 100 pixel absorption map to be collected in times ranging from seconds to sixty minutes. (Longer times may of course be employed for either higher signal-to-noise ratio or for more imaging pixels.) This provides the ability to identify chemical species with nanoscale resolution in the scale of minutes and with high chemical specificity. To distinguish chemical composition from other sample variations, including mechanical and thermal properties and also local sample thickness, it is often desirable to acquire spatially resolved IR absorption maps at two or more wavelengths. This allows two or more maps to be compared to normalize out of the other effects mentioned above resulting in a map that contains contrast more purely associated with IR absorption. Note that it is also possible to extract thermomechanical properties for independent display and analysis. For example the contact resonant frequency can be used to deduce the local sample stiffness, the quality factor Q can be used to determine the sample's viscoelastic properties (for example see "Contact-resonance atomic force microscopy for viscoelasticity" by P. A. Yuya et al in J. APPL. PHYS. 104, 074916 2008). Techniques like those described in the Yuva paper can be implemented into a property inversion algorithms 46 in FIG. 4 and the extracted properties can also be used to generate spatially resolved maps 48 of thermal and mechanical properties of the sample.

Signal Conditioning and Analysis

After the data is acquired and averaged, further processing is generally performed by signal conditioning electronics to produce a high quality signal indicative of the IR absorption of the sample. The signal conditioning electronics may be analog, digital or a hybrid. It may also be distributed among multiple components, for example a Field Programmable Gate Array, a Digital Signal Processor, and a host computer. A common first step is to perform a Fourier transform on the dynamic response. This gives the amplitude (and phase if desired) of the cantilever's response over a range of frequencies. Analysis of the FFT makes it possible to select the range of frequencies that are most sensitive to the IR absorption of the sample. It can also be possible to exclude frequencies that may be more sensitive to background effects. It can be desirable in some cases to store and analyze the entire FFT. Collecting the full deflection data and/or power spectrum allows the optimal selection of frequency bands to be done after data collection or iteratively as the spectra or image is being displayed. Thus the band can be optimized on the vertical or lateral fundamental or higher mode of the cantilever to achieve the optimum resolution and discrimination of the spectra or different components of the sample. In other cases, especially when speed and memory are important considerations, a small portion of the FFT can be analyzed and the results stored and/or displayed as a function of wavelength.

In one embodiment, the inventors have employed a technique that uses the analysis of the FFT on a known material to identify the bands of the FFT that have the greatest correlation to the known IR absorption. These optimal FFT bands can be windowed and/or weighted for use in a more optimal calculation of an absoption spectrum. Identification of such bands can be performed, for example, by partial least squares analyses or more sophisticated chemometrics techniques. Once such a measurement is done on a known sample, the frequency windowing and/or weighting can be applied to unknown materials.

In another embodiment, the inventors have employed a technique that normalizes the cantilever response at a plurality of IR wavelengths by the cantilever's dynamic response at a selected reference wavelength. We shall call this technique Reference Dynamics Normalization (RDN). RDN works in the following way. When the sample absorbs radiation from a pulse, the cantilever responds with a deflection $S(\lambda,\omega)$ that is the cantilever response as a function of radiation wavelength $\lambda$ and frequency $\omega$. Most commercial AFMs measure a signal related to the end slope of the cantilever while other AFMs measure absolute deflection. We will refer to either technique generally by reference to detecting the cantilever motion. This cantilever motion has the following approximate form:

$$S(\lambda,\omega) = \alpha(\lambda) T(\omega)$$

Where $\alpha(\lambda)$ is the samples absorption as a function of wavelength $\lambda$ and $T(\omega)$ is the dynamic transfer function of the cantilever interacting with the sample. The signal $S(\lambda, \omega)$ is the Fourier transform of the cantilever time varying motion $s(\lambda, t)$ as measured by the data collection system.

In the case that the dynamic transfer function $T(\omega)$ is constant over the time of a measurement, it is possible to extract a good signal representing the IR absorption employing the following dynamic normalization technique.

$$\frac{\alpha(\lambda)}{\alpha(\lambda_0)} = \frac{S(\lambda, \omega)}{S(\lambda_0, \omega)} \frac{T(\omega)}{T(\omega)} = \frac{S(\lambda, \omega)}{S(\lambda_0, \omega)}$$

The ratio above is the IR absorption spectrum normalized to a reference wavelength $\lambda_0$. The ratio is constructed by dividing the Fourier transformed cantilever motion $S(\lambda, \omega)$ over the wavelength range of interest and dividing it by the response $S(\lambda_0, \omega)$ at the reference wavelength $\lambda_0$, and also measuring it at a broader range of wavelengths $\lambda$ As long as the dynamic transfer function $T(\omega)$ is relatively constant for the measurements, this term cancels out, thus normalizing for the dynamics of the cantilever. The cantilever dynamics can be quite complex, with multiple mode resonances. This normalization removes from the signal a large number of mechanical effects that are not related to the IR absorption of the sample. The reference wavelength $\lambda_0$ is generally chosen to have a high relative absorption and generally avoids wavelengths with little or no absorption.

Note that it is also helpful to choose ranges of frequencies $\omega$ where the cantilever has an adequately detectable response. It can also be helpful to choose frequency bands that are more sensitive to the tip-sample interaction and less sensitive to background forces, as discussed in the next session. In practice the inventors calculate the ratio $S(\lambda, \omega)/S(\lambda_0, \omega)$ at multiple points $\omega$ in the Fourier transform and then average together the ratio over the frequency band. This averaging further serves to improve the signal to noise. For example, if the FFT calculates sixteen frequencies within a resonance peak, calculating and averaging the ratio $S(\lambda, \omega)/S(\lambda_0, \omega)$ at sixteen frequencies can improve the signal-to-noise by up to the square root of sixteen or four times over measuring the cantilever motion just at the peak frequency. The frequency range employed can be set manually by a user or automatically based, for example, on the signal to noise of the signal at various frequencies.

Figure 14:
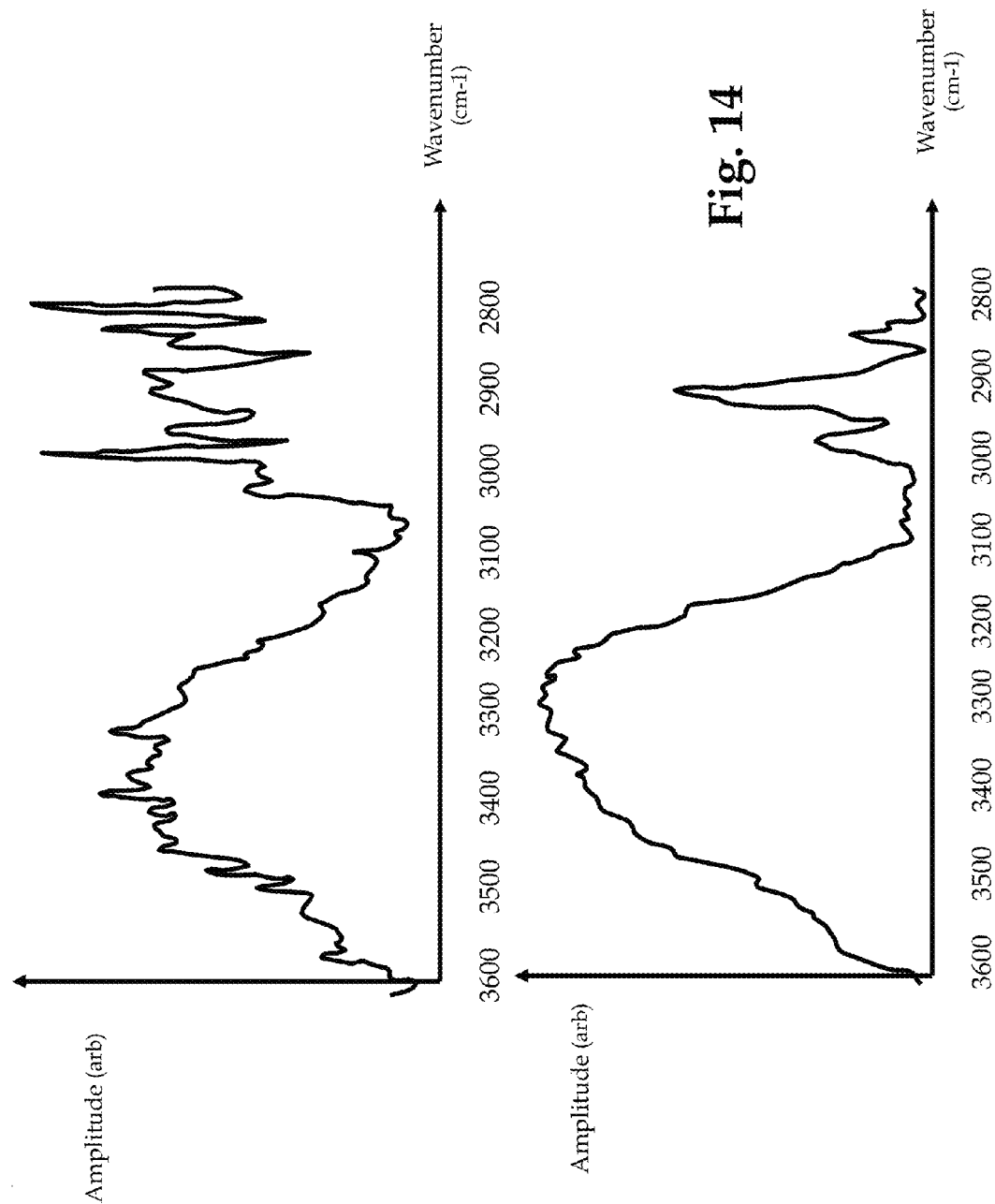
FIG. 14 shows example spectra constructed using FFT peak height, peak area, and Reference Dynamics Normalization.

FIG. 14 shows an example spectrum constructed using Reference Dynamics Normalization. The top plot shows a spectrum corresponding to the peak amplitude of the $2^{nd}$ mode of cantilever motion. The bottom plot shows a spectrum obtained simultaneously by using the Reference Dynamics Normalization technique. Note that in the RDN spectra, the overall noise is much lower and several additional absorption peaks become clear versus earlier techniques.

Alternative embodiments include using a curve fit routine to fit one or more mode resonances. A simple harmonic oscillator model, for example, can be used to fit subsets of the Fourier transformed motion $S(\lambda, \omega)$. The SHO fit can return the base amplitude $A_0$, the quality factor Q, and the mode frequency $\omega_0$. The amplitude $A_0$ will generally be related to the IR absorption. Note, however, that this technique also provides useful information about the mechanical properties of the sample as the mode frequency $\omega_0$ and quality factor Q are sensitive to the mechanical properties at the tip-sample interface. So in addition to IR absorption it is possible to simultaneously obtain nanoscale information about the mechanical properties of the sample. The simultaneous measurement of Q and resonant frequencies also aid in the deconvolution of mechanical effects when spatially mapping the IR absorption for example at a fixed wavelength. Measuring these properties simultaneously with the cantilever amplitude allows variations in mechanical properties of the sample to be disentangled from IR absorption.

Many other analysis algorithms can provide suitable results, for example measuring the amplitude at a specified frequency or integrating the cantilever amplitude and/or phase over one or more mode resonances. It can also be beneficial to employ combinations of vertical motion, lateral motion and/or thermal response to construct a signal indicative of the absorption of the sample.

Alternately, the amplitude, frequency and phase can be extracted by directly analyzing the time varying cantilever signal without requiring a Fourier transform. The time varying signal is generally well represented by a sum of decaying oscillations. Conventional multivariable curve fitting techniques can be employed to find frequencies, amplitudes and decay constants that reconstruct the time varying cantilever signal.

It is often desirable, however, to employ deterministic calculations that will complete in a specified amount of time, as opposed to iterative techniques like curve fitting. One suitable algorithm is Harmonic Inversion, for example, as described V. A. Mandelshtam and H. S. Taylor, "Harmonic inversion of time signals," *J. Chem. Phys.* 107 (17), 6756-6769 (1997). Erratum, ibid. 109 (10), 4128 (1998) and online at http://ab-initio.mit.edu/wiki/index.php/Harminv.

This algorithm uses matrix inversion techniques to find the series of eigenmodes that best represent the time varying oscillation of the cantilever. From this analysis, the amplitude of any selected mode or modes can be used to determine the response to absorbed radiation. Harmonic Inversion can also return the mode frequency and quality factor Q, having the same advantages of mapping mechanical properties as the SHO fit mentioned above.

Empirical Approaches

In addition to the type of deterministic and statistical approaches outlined above, neural nets and equivalent approaches can be used to 'train' the software to recognize the important information contained in the cantilever response. For example, the probe can be placed on model samples with a known spectrum and then excited by a range of IR wavelengths. The neural net can then be given the data that describes the cantilever response and the known spectrum of the model material and it 'trains' so that, when provided with equivalent data, it will produce the correct spectrum. This training will be carried out on a range of model samples all with known spectra so the neural net learns how to provide the correct spectrum when given the data from a wide range of samples including unknown materials. Such neural nets can have a variety of forms and a variety of training strategies are possible as well as testing procedures. Someone skilled in the art will know of these and can try various approaches and select the best on the basis of performance. Neural nets and equivalent method have the advantage that they can model complex behaviors including non-linear behavior. They can be applied to the Fourier transform of the cantilever motion or to motion without Fourier or other transform or both can be included in the training data. The probe, during training and measurement, can be used in contact mode or any form of dynamic mode including force distance curves, tapping mode etc. The pulsing regime of the laser can also be of any form; it might be at the resonant frequency of the probe while in contact, it might be fast relative to any dynamic motion or slow, it might be that the laser pulse is triggered by some aspect of the cantilever behavior or position or that the movement of the probe is triggered by the laser pulse. In each case the objective is to identify the characteristic behavior that provides the greatest amount of information on the absorption behavior of the sample. These approaches and can be used in concert with deterministic and/or statistical processing of the data; for example, where data are gathered with the probe above the sample (not in contact) then in contact, such as when performing force distance measurements, then preprocessing of the data using the relative cantilever transform functions (see below) or some other preprocessing might be used.

Accounting for Local Topography

One factor that can influence the response of the probe it the topography of the sample local to the tip. The probe can be used to determine the topography of the sample and that part of it local to the probe tip can be extracted and represented as a series of x, y and z coordinates where, for example, the 0, 0, 0 position in x, y and z is taken to be the point of contact of the probe. The extent of the topography data can be decided upon by the experimenter and would be, typically, data that describes the topography up to a 500 nm radius around the tip of the probe. A multivariate model can then be built from this data to compensate for the effects of topography so that the model provides, regardless of the actual topography of the sample in the immediate vicinity of the probe, the spectrum that would have been obtained on a perfectly flat surface. Neural nets can also be used for this type of application.

Background Reduction

There are several sources of potential background effects that can contaminate PTIR spectra. The first is absorption of energy by the AFM cantilever and/or tip. Common AFM cantilevers are fabricated using micro-lithography methods out of materials such as silicon and silicon nitride. These materials absorb IR radiation at certain wavelengths. So if such a cantilever is exposed to the laser pulse, the cantilever itself will experience a rapid expansion shock, and it can be difficult to separate out the data due to the sample from the cantilever itself expanding and the corresponding induced ringing.

Background Reducing Probes

Figure 15:
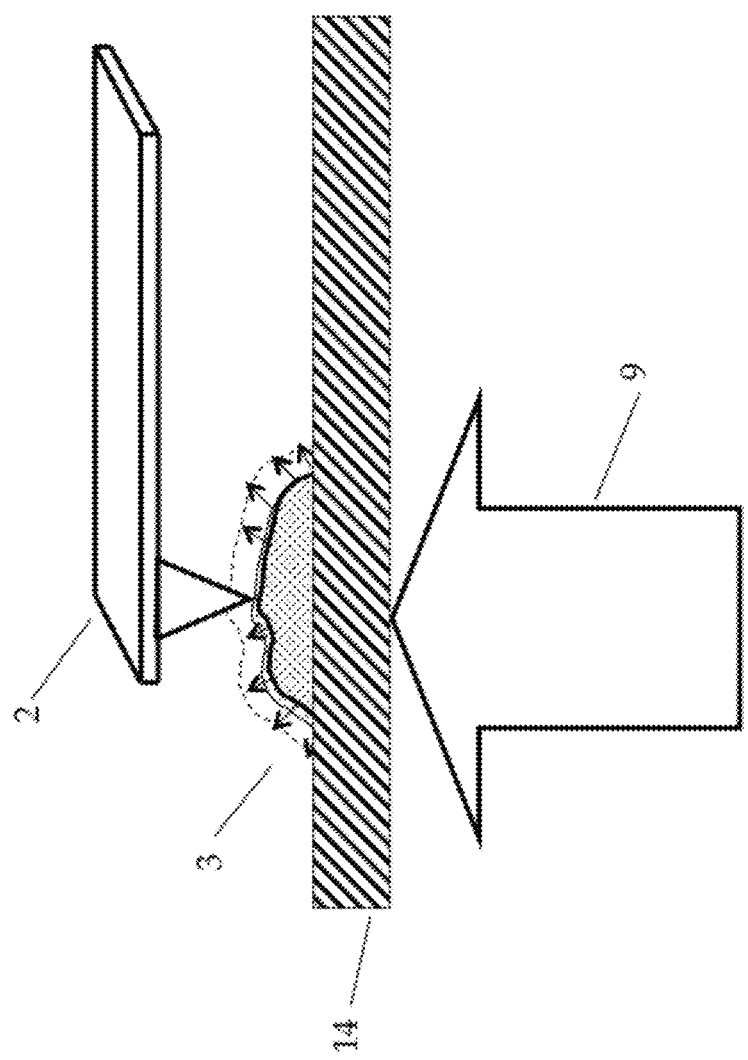
FIG. 15 shows a schematic of an illumination geometry enabled by use of an IR transparent cantilever.

One solution is to make the cantilever either all or in part of a material that is suitable from a mechanical standpoint for use as an AFM probe, but is also transparent in the IR. For certain wavelength ranges in the mid-IR, silicon cantilevers are highly transparent and provide minimal background. Other materials such as sapphire, heavy metal fluoride glasses and chalcogenide glasses may provide suitable materials. Also a number of glass, typically silica, probes have been developed for use as AFM probes. As shown in FIG. 15, a transparent cantilever 2 allows for an alternative geometry. If the sample 3 is mounted on an IR transparent substrate 14, such as ZnSe, then the IR illumination 9 may pass through all elements with only absorbent regions of sample 3 actually absorbing any significant amounts of IR energy.

Another potential solution top down illumination is to make all or part of the cantilever reflective in the IR, to avoid absorption. The inventors have found that coating the lever with gold can minimize absorption by the cantilever. Typically the coating needs to be thick enough to prevent significant absorption which can cause the end radius of the probe to be large. This may require that the probe be fabricated from the reflective material as opposed to a coating. A number of designs have been developed which incorporate metallic probes on cantilevers including sharpened metallic wires.

Figure 16:
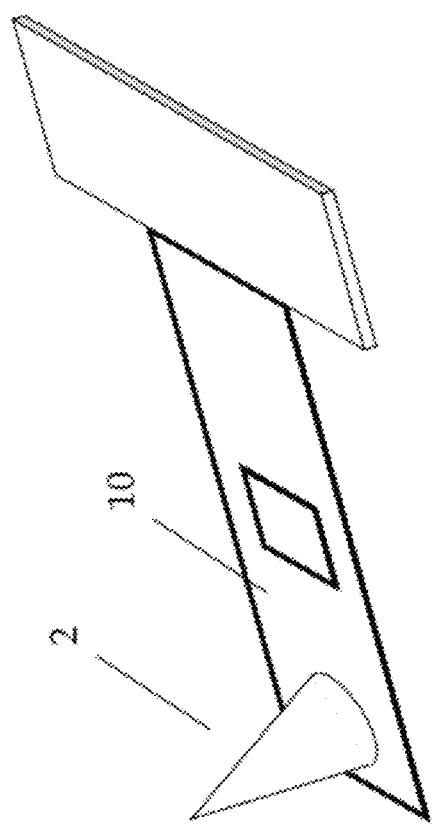
FIG. 16 shows a schematic diagram of a cantilever with an opening to allow transmission of an IR beam and/or enhancement of higher order oscillation modes of the cantilever.

One innovative probe for background reduction is shown in FIG. 16. This probe contains an opening 10 somewhere along the length of the cantilever. The opening can serve two separate purposes. First it can serve to provide optical access for the IR beam to be delivered from the top side of the sample. In this case the IR beam can be directed through the opening and onto the sample, enabling minimal or no absorption by the cantilever.

Second, it can be used to amplify the sensitivity of a harmonic of the cantilever's flexural oscillation, as described by Sahin in U.S. Pat. No. 6,935,167. As will be discussed below, higher order modes of the cantilever oscillation can be less sensitive to background forces, so placement of an opening in the cantilever can increase the signal-to-noise for selected higher order modes chosen to suppress background signals.

Another possibility is to use a tuning fork probe. These probes lack a cantilever and so interaction with the cantilever of materials remote from the tip cannot occur (see the next section for a detailed description of this phenomenon). The position of the tip of the probe above the surface is governed by the response of the tuning fork as the tip gets very near to the surface. In some experiments, when the laser power is high, the expansion of the sample will bridge this gap and this will be sensed by the probe. Alternatively, the probe can be driven into the sample prior to the laser pulse and any induced ringing will be a measure of the IR radiation absorbed by the sample. The tuning fork probe could be made out of IR transparent materials etc. as indicated above.

Optimal Mode Selection

Another source of potential background due to the absorption of IR radiation by the sample and where a portion of this energy is re-radiated to the body of the cantilever as a pressure wave. This effect is shown schematically in FIG. 17a. The result of this effect is that the AFM probe can sense IR radiation of the sample over a much larger area than just the tip-sample contact area. In the worst case, this background force can be sensed over the entire surface area of the cantilever, dramatically degrading the resolution of the technique. The inventors have developed strategies to counter this problem.

Figure 18:
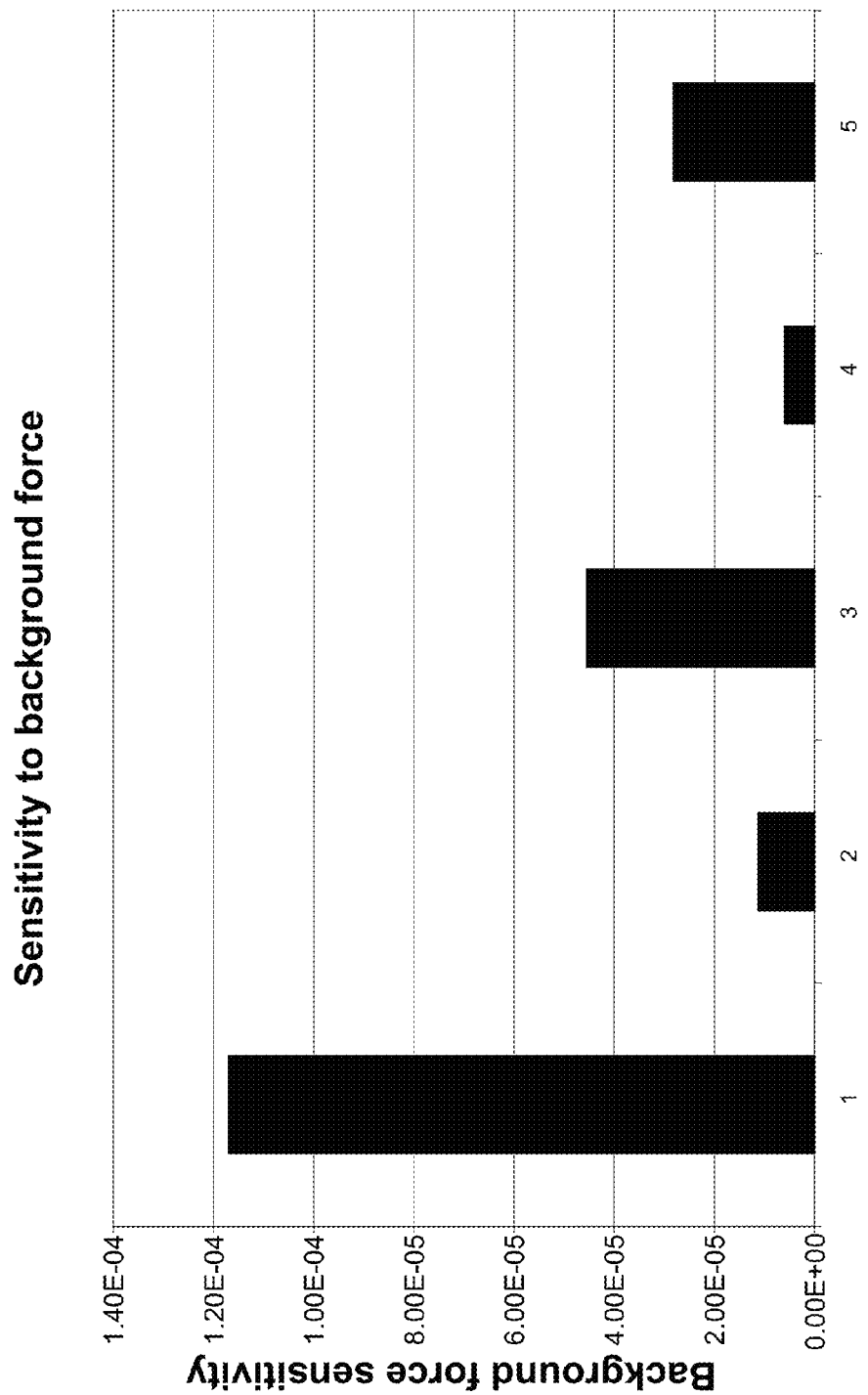
FIG. 18 shows the relationship between resonance mode and background sensitivity for the first few modes of a cantilever's flexural oscillation.

First, the inventors have determined that the sensitivity to this background force is lower for certain modes of oscillation. The first two modes of oscillation are shown in FIG. 17b. The fundamental vertical deflection mode is most sensitive to background forces because forces anywhere along the cantilever increase the amplitude of this mode. For higher order modes of oscillation, the mode shape consists of part of the cantilever deflecting upwards and part downwards. The background forces that act along the entire cantilever tend to be averaged out to some degree for these higher modes, reducing their sensitivity to unwanted forces. And specifically, symmetric modes of oscillation, for example the $2^{nd}$, $4^{th}$, $6^{th}$, and higher even number modes are most effective at reducing sensitivity to this background. A plot of the relative sensitivity to background forces is shown in FIG. 18. For this reason the inventors usually select a mode other than the fundamental, often selecting the $2^{nd}$ mode which offers much better background rejection and usually sufficient signal to noise.

Transfer Function Adjusted Background Subtraction

The inventors have developed another means of directly subtracting background signals. The absorption $\alpha_c(\lambda)$ sensed by a cantilever in contact with the sample surface comprises two terms:

$$\alpha_{tot}(\lambda) = \alpha_t(\lambda) + \alpha_b(\lambda)$$

Where $\alpha_t(\lambda)$ is the absorption of material directly in contact with the AFM tip and $\alpha_b(\lambda)$ is the absorption of surrounding material that generates a force over a surrounding area of the cantilever. There is somewhat of a challenge decoupling these effects. The background absorption $\alpha_b(\lambda)$ can be measured in principal by lifting the tip slightly off the surface so that the only forces that are felt by the cantilever are the background forces. The challenge is that when the cantilever is lifted off the surface, the cantilever dynamics change dramatically. So it is generally not sufficient to simply subtract a spectrum with the cantilever on the surface from one off the surface. Instead, the inventors have employed the following relationships. The measured response of the AFM cantilever $S(\lambda,\omega)$ is given roughly by:

$$S(\lambda,\omega) = T(\omega)\alpha(\lambda)$$

Where $T(\omega)$ is the cantilever's dynamic transfer function, i.e. its mechanical dynamic response to a given input force as a function of input frequency $\omega$. Note this term includes the tip's interaction with the sample surface. When the tip is in contact with the surface, the cantilever's response is given by:

$$S_c(\lambda,\omega) = T_c(\omega)\alpha_{tot}(\lambda)$$

When the tip is off the surface, the free cantilever response is given by $$S_f(\lambda,\omega) = T_f(\omega)\alpha_b(\lambda)$$

Note that in general $T_c(\omega) \neq T_f(\omega)$, since the cantilever's dynamic response changes when the boundary conditions change between the free cantilever and the one with the cantilever touching the surface. Now the signal we wish to extract is the spectrum $\alpha_t(\lambda)$, the spectrum of the material under the tip and not including the background force. This signal can be obtained by the following relationship:

$$\alpha_t(\lambda) = \lambda_{tot}(\lambda) - \alpha_b(\lambda) = S_c(\lambda,\omega)/T_c(\omega) - S_f(\lambda,\omega)/T_f(\omega)$$

In words, this relationship just says we measure the cantilever's response on and off the surface and divide by the relative cantilever transfer functions for the contact and free conditions. The cantilever's transfer functions in these two conditions can be measured in a variety of ways. For example, it can be measured by using a mechanical transducer that excites the cantilever. Such excitation could be a pulse, a chirp, a sinusoidal sweep, for example, or any other wave pattern capable of exciting motion of the cantilever into detectable motion. The resulting background corrected spectrum $a_t(\lambda)$ is generally calculated at one or more frequencies w where the cantilever has sufficient dynamic response to be detectable by the cantilever detection system. In fact, it is generally advisable to calculate $\alpha_t(\lambda)$ at multiple frequencies and average the results to improve the signal to noise. Note that it is completely equivalent to average together $\alpha_t(\lambda_i)$ over a range of frequencies $\omega$ and then repeat this for different values of $\lambda_i$ to assemble a spectrum.

Heterodyne Detection

Heterodyne techniques may also be employed to reduce background sensitivity. In this case, an additional modulation signal is added to modulate the interaction between the tip and sample. Small modulation of the tip-sample interaction can cause substantial changes in the cantilever motion excited by the IR absorption, for example by changing the contact area, coupling efficiency and/or boundary conditions of the cantilever. But these changes in tip-sample interaction usually result in only minor changes in the average distance between the cantilever body and the sample and thus result in negligible changes in the background force. Thus a modulation can be applied that significantly modifies the response to IR absorption under the tip and has very little impact on the cantilever's response to background forces which are not local to the tip. The net impact of this modulation is to create a signal that is highly localized to the tip, providing resolution limited only by the tip/sample contact area. This resolution can be as small as a few nm, and far smaller than the diffraction limits of conventional IR microcopy.

The modulation of tip sample interaction may be provided for example by a piezoelectric element which modulates either the probe or the sample position. Such piezo devices are used for example to excite cantilever oscillation for Tapping Mode or other oscillating cantilever techniques or used for techniques like Force Modulation. The cantilever modulation can also be provided by thermal excitation, electrostatic excitation, acoustic excitation or other techniques that modulate the tip sample interaction and/or probe sample distance. Any of these modulation techniques can be integrated directly into the cantilever. Commercially available self-actuated cantilevers are available from Veeco Instruments, and thermally actuated cantilevers have been demonstrated by many university and industrial researchers.

There are several ways in which a heterodyne technique can be applied. In one embodiment, the additional modulation is applied at frequencies slower than the repetition rate of the IR source. In this case the envelope of the cantilever response will be modulated by the applied heterodyne modulation. So if the laser repetition rate is 5 kHz, for example, the modulation could be applied at 500 Hz. As the cantilever ringdowns are recorded, the amplitude of the signal directly from the tip will be modulated at 500 Hz. Using Fourier, lock-in or other filtering techniques, the force from the area directly under the tip can be isolated. Thus the IR absorption from a much more localized region can be extracted. In the simplest implementation of this technique two or more spectra can be obtained at different setpoint forces and the resulting spectra can be subtracted. The differential spectrum is the result primarily of forces felt by the AFM tip and not background from the cantilever body.

Another means of applying this technique is to modulate the tip-sample interaction in sync with the pulses from the IR source. In one embodiment, the tip-sample interaction can be modulated back and forth between two interaction values. Each alternative cantilever ringdown will correspond to the response at each of the alternating interaction values. Note that it is also possible to alternate the tip-sample interaction after an arbitrary number N of ring downs cycles. By looking at response of the higher interaction ringdowns versus the lower force ringdowns it is possible to isolate a portion of the signal that is confined to the tip-sample area.

Note that such a signal can be generated easily with the data acquisition electronics described elsewhere in the document.

In the case of alternating the interaction after every ringdown, the data acquisition window can be set to be large enough to cover two successive ringdown events. The two adjacent ringdown events can be synchronously averaged as previously described. After averaging is complete, the two ringdown events can be separately analyzed to extract information about amplitudes, mode frequencies, phase. Alternately, if the interaction is modulated after N ringdowns, the N ringdowns for each interaction force level can be averaged together and this process can be repeated for the second interaction level. It is also possible to directly accumulate the difference between responses at the two interaction forces. In this case all the ring downs at one interaction level can be added to the accumulating buffer and all the ringdowns at the other interaction level can be added to the accumulating buffer. At the end of the accumulation period, the resulting data represents the difference in response to the IR radiation at the two tip-sample interaction levels.

Any of these signals can then be compared at the two interaction values to create a differential signal corresponding to the force felt substantially from the apex of the tip, dramatically reducing the sensitivity to the background.

It is also possible to employ the feedback system of the AFM to create a differential measurement. In this embodiment, cantilever response versus wavelength can be measured at two or more setpoint force levels. Changing the setpoint can modulate the amplitude of the response to the IR radiation and once again the change is primarily due to the force changes at the tip apex. Subtracting or otherwise creating a differential measurement between cantilever responses at different setpoint forces can dramatically improve the spatial resolution of the PTIR technique.

Phase Selective Detection

The problem of screening out the effects of IR absorption not local to the tip can also be addressed using phase selective detection. Consider the case in which two IR absorbing regions are a distance d um apart. If we place the tip directly on top of one of the regions, the cantilever will receive a force almost instantly following the absorption of the IR radiation. The impulse from the neighboring region will arrive a time $\Delta t = d/v$ later, where v is the speed of sound in the material. Assuming a sound velocity of 2000 m/s, a pulse originating from a distance d=1 um from the tip will arrive 0.5 nsec later than the pulse originating under the tip. Looking at a mode resonance at 5 MHz, this would result in a phase delay between the two signals of approximately 1 degree, a level that is easily detectable with commercial electronics or with digital FFT algorithms. For example, commercial lock-in amplifiers are available from Stanford Research, for example the SR844, with a phase sensitivity of 0.02° and a bandwidth of 200 MHz. With this phase sensitivity it is possible to discriminate the time delay between absorbing regions with a spatial resolution of around less than 100 nm. In this mode of operation, the cantilever amplitude and phase is calculated as a function of source wavelength. The IR absorption spectrum can then be corrected when the phase signal suggests that the absorbed pulse originates away from the tip-sample contact point.

Reduction of Background by Probe Movement

If the tip is on top of a body absorbing radiation then it will be excited by the expansion of this body as a consequence of it absorbing the incident IR radiation. If there is an adjacent body, separate from the one beneath the tip, then it might also be excited by the elastic wave emanating from this object when it absorbs IR radiation. To remove this unwanted contribution, the probe can be moved in a circular manner, describing, for example, a 5 nm circle, rotating slowly relative to the rate of the laser pulses. When the probe encounters an elastic wave from the adjacent body as the probe, because of its circular motion, is moving toward it, the energy of the encounter will be increased by the motion of the probe. Similarly, as it travels away and it encounters a similar wave, the energy will be less. As a consequence, the total energy transfer to the probe will be modulated at the frequency of the periodic motion of the probe. When the probe stops rotating and moves to the middle of the circle, there will be no modulation. Calibration using model samples of known structure will enable a relationship between the amplitude of the modulation while the tip is moving and the energy imparted to the probe when it is stationary to be empirically determined. This relationship can then be used to correct for that part of the energy coming from the adjacent body so that the energy coming from only the object beneath the tip can be calculated.

Measurement of Temperature Change

When IR radiation is absorbed by a region of a sample the region is rapidly heated, raising the local temperature. A tip placed in contact or near contact with the sample surface will also increase its temperature. Sensing the tip temperature as a function of wavelength of incident radiation can also be used to generate absorption spectra. To sense the probe temperature, the inventors have employed AFM probes with a temperature sensing element one or near the probe tip. Suitable temperature sensing elements include thermocouple junctions, metal films, semiconductor sensors or other thermal sensing devices that change voltage, current and/or resistance with temperature.

Temperature sensing has several advantages. In the case of IR absorption over a large area, one runs the risk that the impulse felt by the AFM tip is the result of elastic waves that originate from IR absorption in area somewhat distant from the tip. In this case the lateral resolution of the AFM based IR technique can be degraded. Thermal propagation however, is much slower than the propagation of elastic waves. Therefore, measuring changes in the tip temperature can provide an alternative or additional signal to enhance the resolution of the technique.

Temperature measurements can be accomplished with thermal sensing AFM probes. Suitable probes have a temperature sensing element built into the cantilever and/or probe tip. The temperature sensing element may be a thermistor, thermocouple or other element that changes a measurable property with temperature. Thermocouples have been integrated with AFM cantilevers using a junction of two metals near the probe tip. Many varieties of thermistors have been constructed on AFM cantilever probes using for example metal films and/or semiconducting materials. Such devices are described, for example, in publications by the research groups of Prof. Arun Majumdar, Prof. William King and Prof. John Weaver. Some of the probe designs, including those developed by Dr. King may be electrically heated by passing current through the probe arms. Such probes are decided in copending application Ser. No. 11/405,772, now U.S. Pat. No. 7,497,613. The use of such probes also enables mapping of thermal properties of the sample in addition to the IR absorption. As mentioned previously, the independent measurement of thermal properties can aid in deconvolving the IR absorption from other thermomechanical properties that contribute the probe response.

A sensitive amplifier is typically used to detect and amplify voltage or resistance changes in the probe as a result of temperature change. The inventors have employed several different amplifiers successfully. The most common amplifier type is a bridge type arrangement, for example a Wheatstone bridge. In this case, one resistor in the bridge is used to adjust the amount of current flowing through the cantilever probe, thus setting its steady state temperature and its sensitivity. A second resistor on the opposite side of the bridge is usually tuned to roughly match the resistance of the probe. The voltage difference between the probe and the reference is typically amplified by one or more gain stages. As an alternative to the bridge circuit, a current source can be used to control the current flow through the probe.

The inventors have also used transformer amplifiers which are increasingly sensitive to dynamic changes in the signal and can provide excellent sensitivity to transient effects such as the temperature change resulting from an IR pulse. These amplifiers have been described for example in U.S. Patent Application Publication US 2006/0289510 A1 and by Hammiche et al in Journal of Microscopy 213 pp 129-134. It is also possible to use very simple electronics, for example a simple voltage divider that is then AC coupled into an amplifier. Many other circuits known in the art can provide suitable detection and amplification of the probe resistance change.

It can be advantageous to arrange for fast time response to detect the temperature increase at the tip primarily due to IR absorption by material close to the tip contact point. For this reason the inventors have employed high bandwidth amplification electronics for some experiments a bandwidth exceeding 100 MHz.

The use of probes with integrated heaters and temperature sensing probes have another advantage. It allows simultaneous and/or sequential measurement of the thermal properties of a sample. So with the same probe and AFM setup it is possible to measure IR absorption, thermal conductivity, thermal diffusivity, and/or thermal expansion. These capabilities, for example, are available on NanoThermal Analysis and Scanning Thermal Microscopy products market by the assignee of this application, Anasys Instruments. This combination of measurement capabilities provides added information to help users measure, map, and distinguish closely related materials. The integrated heater in these probes also provides the ability to rapidly ramp local regions of the sample and measure the change in chemical properties of a sample as a function of temperature. No other technique to our knowledge allows spectroscopic information to be obtained on the nanometer scale at variable temperatures.

Combining optical absorption measurements with thermal expansion measurements, such as described in co-pending application Ser. No. 11/405,772, now U.S. Pat. No. 7,497,613, can assist in analysis of the local absorption properties of the sample. In this case the probe, or possibly a second probe, would be of a thermally controlled type such as described on the co-pending application, and making thermal expansion measurements along with absorption measurements. It is possible that these can be sequential measurements or they can be simultaneous measurements. It has been demonstrated that the resonant signal can be seen in probes that can also measure the local temperature of the sample surface. This has the benefit that the absorption can be measured both by the resonant signal and by the local temperature rise of the sample surface. The combination of these two measurements as well as the possibility to measure the local thermal conductivity and thermal diffusivity of the sample with the thermal probe can improve the quantification of the signal as well as reduce potential artifacts. An example of this is demonstrated by the case where the probe is scanned across the sample surface at a fixed wavelength. The resonant signal can vary in amplitude due to variations in material that absorb the radiation of interest but can also vary due to variations in thermal conductivity in underlying layers causing reduced rapid expansion and therefore reduced resonant signals. Another factor that can cause variation in the absorption signal is the change in Young's modulus over the surface of the sample. The material can have similar chemical characteristics but due to the structure of the material (amorphous or crystalline) would have a different modulus. This will definitely impact the frequency of the induced oscillation in the cantilever and may impact the amplitude. Due to this, it may be beneficial to map the modulus variation across the image and also use this as a correction factor.

Resolution

Figure 19:
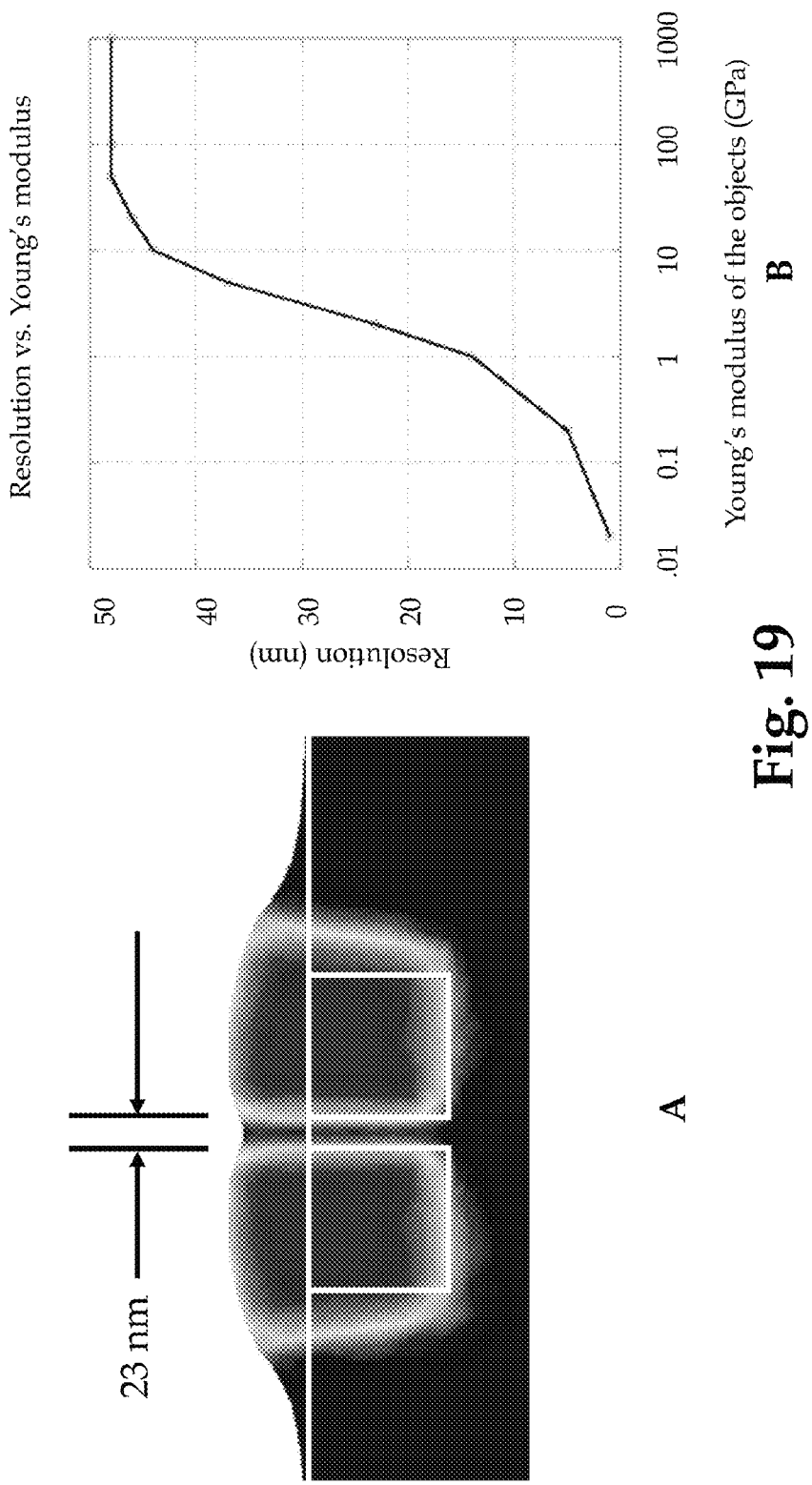
FIG. 19 shows simulation data demonstrating the origin of sub-um resolution.

The resolution enabled by either the PTIR (induced resonance) or thermal detection dramatically exceeds that of traditional IR microscopy tools. This resolution is demonstrated in simulation data shown in FIG. 19. In this simulation, two square IR absorbing regions were placed less than 1 um apart with a non-absorbing material in between and surrounding the absorbers. For this model, the nonabsorbent material was given an elastic modulus of 2 GPa and the absorbing material an elastic modulus of 3 GPa. A contrast criteria was employed to determine the effective spatial resolution. To do this, the temperature of the absorbing regions was rapidly increased and the resulting surface deformation was simulated and the relative height change of the absorbing versus non-absorbing region was measured. FIG. 19A shows the relative temperature (from the shaded intensity) and surface deformation (shape of the top edge). This image shows one case in the simulation corresponding to a separation of 23 nm. Note that that even at this small separation there are clearly visible differences in the temperature and surface deformation between the absorbing and non absorbing regions. To quantify the resolution, the separation between the two absorbing regions was adjusted until the surface deformation over the non-absorbing region was at least 25% lower than absorbing region. The resolution is defined as the separation at which the model shows this 25% change in surface deformation. FIG. 19B shows a plot of expected resolution versus the elastic modulus of the absorbing material. Note that in all cases, the predicted resolution is under 1 um, and in fact under 50 nm. This means that in practice for many materials the resolution of the PTIR technique can be limited only by the tip-sample contact area.

Figure 24:
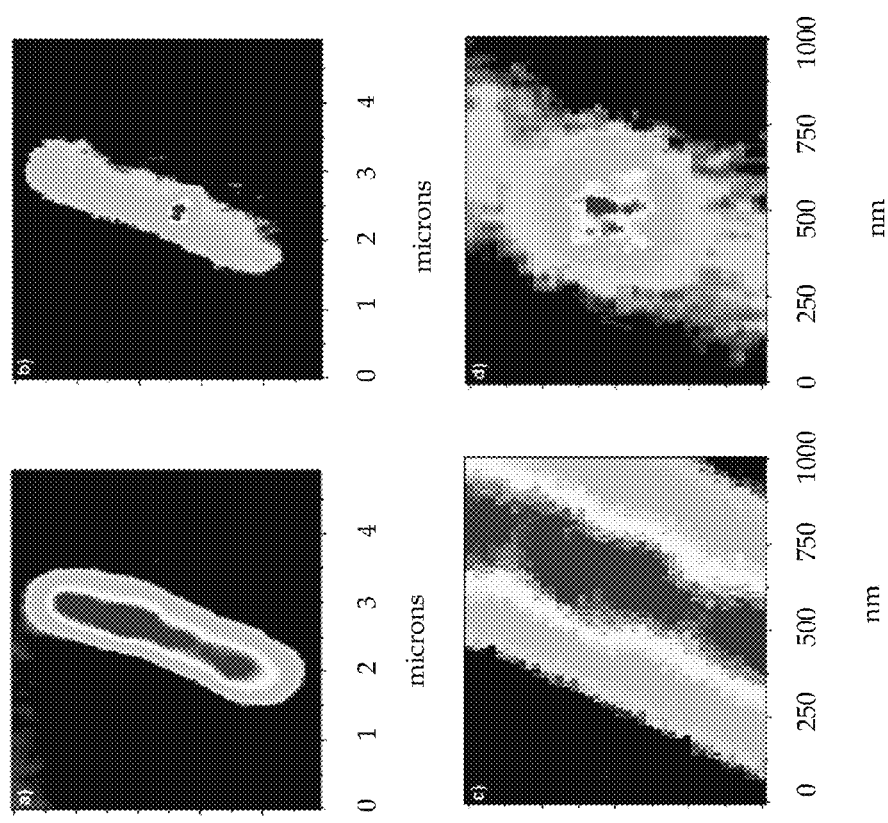
FIG. 24 shows chemical mapping data demonstrating sub micron resolution of a virus inside a bacterium.

FIG. 24 shows actual measured data by the PTIR technique demonstrating sub-micron resolution. This image shows topographic and chemical mapping of a viral DNA inside a bacterium. The presence of the virus can be clearly seen in the chemical mapping images at right, obtained using the AFM-based PTIR technique. The bottom images show zoomed in views, making it clear that the zone of IR absorption is smaller than 200 nm.

Post-Processing

After data collection and signal conditioning, it is often desirable to perform post processing analyses on the IR absorption spectra. These analyses can include baseline correction, identification of peak locations, peak heights, and/or peak widths. Physical models can be used compensate for the dynamic heat flow in the sample, the resulting thermal expansion of the sample material and the transfer of impulse energy to the cantilever. The use of such models can be used to transform the AFM measured spectra such that they better match to reference spectra in FT-IR material databases. Deconvolution of individual peaks may be used to determine specific chemical and structural information about a region of a sample. Post processing may also include reformatting the data such that it can interface with a materials database and a materials search engine. Search engines such as Bio-Rad's Knowitall can be used to compare the AFM-based spectrum of an unknown material against reference spectra. Or for known components in a composite sample it may be sufficient to detect the presence of a specific absorption band, for example an amine or a carbonyl absorption that can be used to distinguish between multiple components. Any of these techniques can provide specific chemical identification and mapping with nanometer scale resolution.

Chemometric Analysis

One of the modes of operation described earlier is spectral mapping where the IR source is fixed to a specific wavelength and then the AFM is used to spatially map the absorption at that wavelength. Chemometric analysis can be used to further enhance this type of measurement. Chemometrics in one incarnation is the identification of the signals that vary most strongly with variations in chemical composition. For example, in the case of a sample with multiple components, chemometrics can be used to identify the intersection of cantilever frequencies and IR source wavelengths that provide the most contrast between the different components. After such an analysis, the system can be set to look preferentially at those frequencies and wavelengths and/or component maps can be created that optimize the contrast between dissimilar materials. The distribution of materials can then be mapped with higher sensitivity and resolution.

Signal Enhancing Substrates

Figure 20:
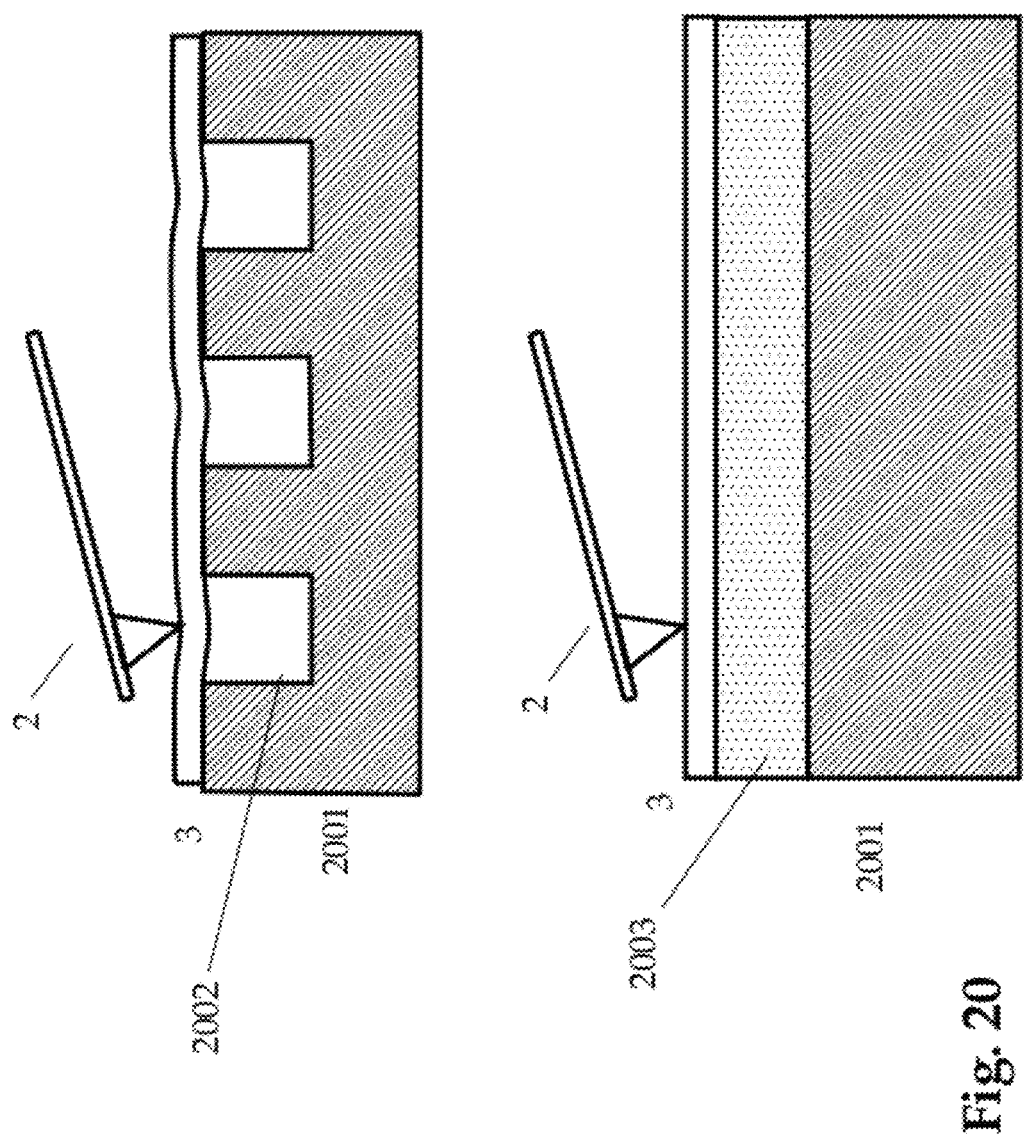
FIG. 20 shows a simplified schematic diagram for the enhancement of signal strength by placing the sample on an insulating substrate to reduce the thermal conduction of absorbed IR energy away from the sample.

FIG. 20 shows simplified schematic diagrams of two techniques for increasing the PTIR signal. In this case, a sample 3 is mounted on a substrate 2001 that has features designed to reduce the thermal conduction between the sample and the substrate. As a reminder, in PTIR IR radiation is absorbed by sample 3 resulting in heat absorption in the sample. The resulting temperature rise depends on many factors including the conduction paths out of the sample. By reducing the conduction path from the sample to the substrate it is possible to engineer a larger temperature increase in the sample. This can result in a larger thermal expansion signal or a larger directly detectable surface temperature. Two techniques for achieving this goal are shown in FIG. 20. In FIG. 20a one or more cavities 2002 are arranged underneath the sample. If the depths of these cavities cavities are kept shallow, e.g. roughly less than the wavelength of IR radiation, IR radiation can still couple evanescently into the sample. But IR radiation absorbed in the sample is deprived of a direct conduction path to the substrate below thus increasing the temperature and thermal expansion signals. In FIG. 20b, a thermally insulating layer 2003 is placed on top of the substrate 2001. Thermally insulating layer 2003 is typically chosen to be at least partially transparent to IR in a region of interest for the sample under study and yet lower in thermal conductivity than the substrate 2001.

Applications

In this section we will outline some of the applications enabled by AFM-based infrared spectroscopy. As mentioned in the previous section, a key application is the identification of unknown materials with sub-micron resolution. The identification of unknown materials is a critical need for research and industry. It is used for example in the development of novel materials, in reverse engineering, process engineering, failure analysis, in forensics, and drug development to name a few. All of these areas currently employ either bulk IR spectroscopy and/or IR microscopy. These tools, however, have no ability to map and identify materials at the nanoscale. The techniques described in the current application enables unknown material identification at the nanoscale using IR absorption spectroscopy. For the purpose of material identification, it is often desirable to compare a PTIR spectrum to those in a reference library. Many commercially available software packages allow the comparison of spectra and suggest candidate materials based on the quality of the match between the reference spectrum and the experimental spectrum. Because the current method and apparatus can measure spectra with sub-micron resolution, it is also possible to identify material locally with sub-micron resolution.

In addition to local material identification, AFM-based IR spectroscopy and imaging can serve as an essential tool for research, process development and/or quality control. Conventional IR spectroscopy is a benchmark tool used to determine the chemical makeup, structure, processing history and other properties of polymers. AFM-based IR enables sub-micron spatial mapping of multiple components in a composite system, for example in multi-component polymer systems. These techniques enable the discrimination and mapping of amorphous versus crystalline phases in polymers and pharmaceuticals. It also provides the ability to distinguish various polymorphs of drugs with nanoscale resolution. It allows the spatial mapping of active components of drugs versus excipients to aid the development and manufacturing of drug release formulations. It can allow inspection of drugs coatings on critical surfaces for example drug coated stents. In fact the technique is in general sensitive to materials on a sample surface and can be used to measure properties of in-situ coatings without special deprocessing.

IR Tagging of Molecules for Spectroscopic Detection

For biomedical and life sciences applications, it is possible to use AFM based PTIR techniques to localize specific molecules in tissue, cells, viruses and other biological materials according to the IR absorption signature of the molecule. Localization of such molecules with sub-um resolution can provide critical insights for biomedical discovery and life sciences research. Applications include localization of drugs within a target cell or tissue, local observation of metabolic activity, detection of pathogens and/or disease.

Figure 22:
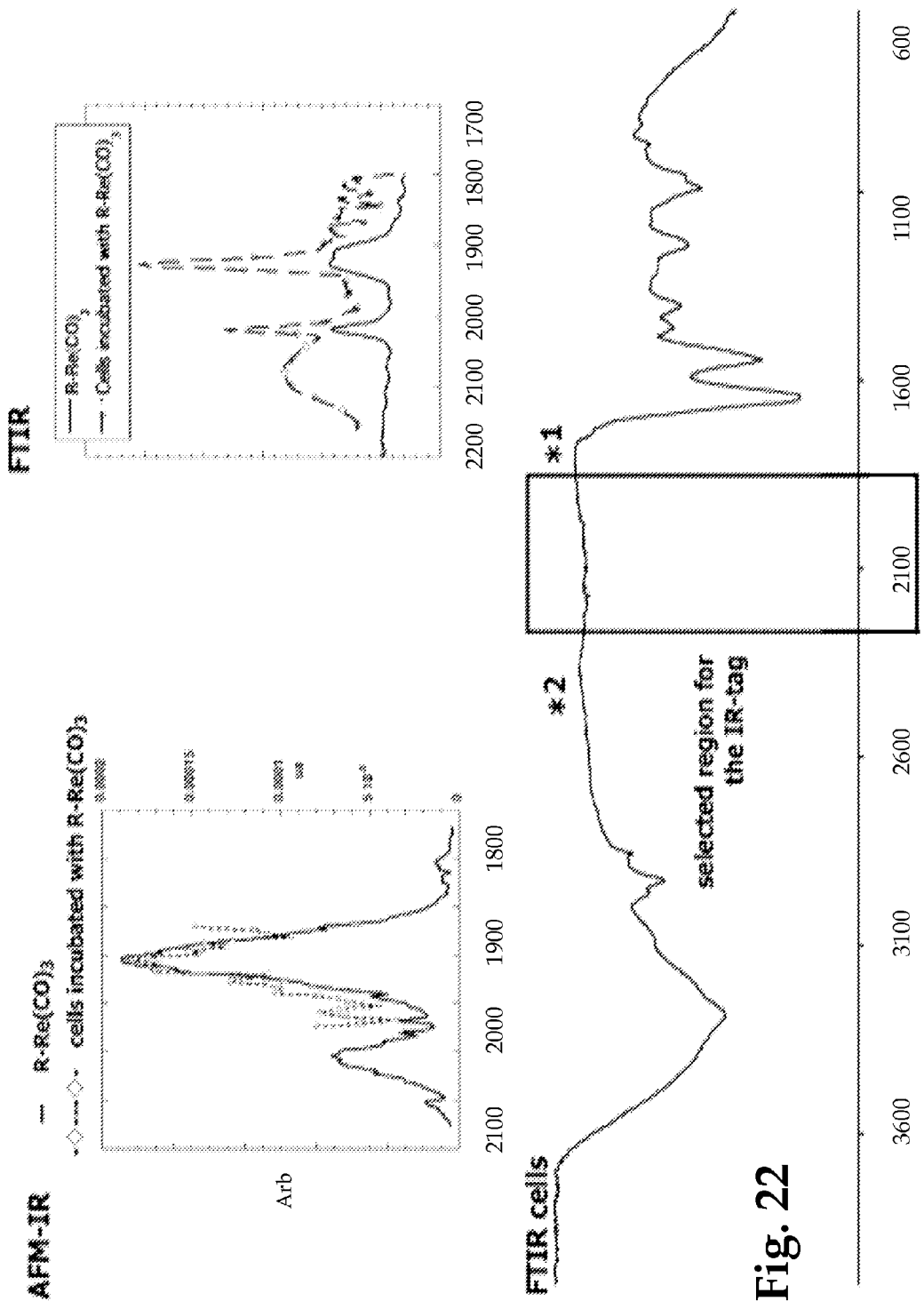
FIG. 22 shows example measurement spectra where tagged molecules are detected inside a cell using an IR absorbing tag.

IR absorbing markers can also be added to molecules to increase the sensitivity of the imaging technique. For example, the inventors have employed a carbonyl group that was chemically added to a small molecule of interest and then set the IR source wavelength to an absorption band of the carbonyl. An example of such a measurement is shown in. FIG. 22 where the absorption at 1904 $cm^{-1}$ was used to map the location of hormones inside a cell, enabled by tagging the hormones with carbonyl groups. This technique provides the ability to tag and visualize the spatial distribution of small molecules that cannot be effectively labeled with other techniques like optical fluorescence. This advantage is enabled by the fact that the addition of only small reactive groups comprising for example a few atoms per molecule can enable a detectable IR absorption. Thus it can be possible to tag a molecule for detection without substantially affecting the function or behavior of the target molecule. IR absorbing markers can also be used to allow detection of exogeneous molecules, (i.e. externally introduced molecules, for example drugs) and also tagged biomolecules. IR markers can be chosen to display an intense absorption band in a region away from common absorptions of biological material. Such a choice allows the absorption of tagged molecules to stand out against the background of untagged biological materials. In one embodiment, the inventors have targeted the 1900-2200 $cm^{-1}$ region, as indicated by the rectangular box in FIG. 22. Metal-carbonyl and azide are chemical groups that have strong absorption in this region without typical absorption by biological material. As such, carbonyl and azide chemical species can be used to functionalize target molecules of interest. Suitable functionalization chemistries are described for example in Salmain, M., Vessieres A., Jaouen G., Anal. Chem. 1991, 63, 2323-2329 and Hillard, E. A., Vessières, A., Top, S., Pigeon, P., Kowalski, K., Huché, M., Jaouen, G., J; Organomet. Chem., 2007, 692, 1315-1326. Note that the tagged molecules can also be chosen such that they bind primarily with targeted structures or molecules within a cell. Thus the use of tagged molecules allows the IR-AFM imaging to be used to map intracellular structures with sub-micron resolution.

Figure 21:
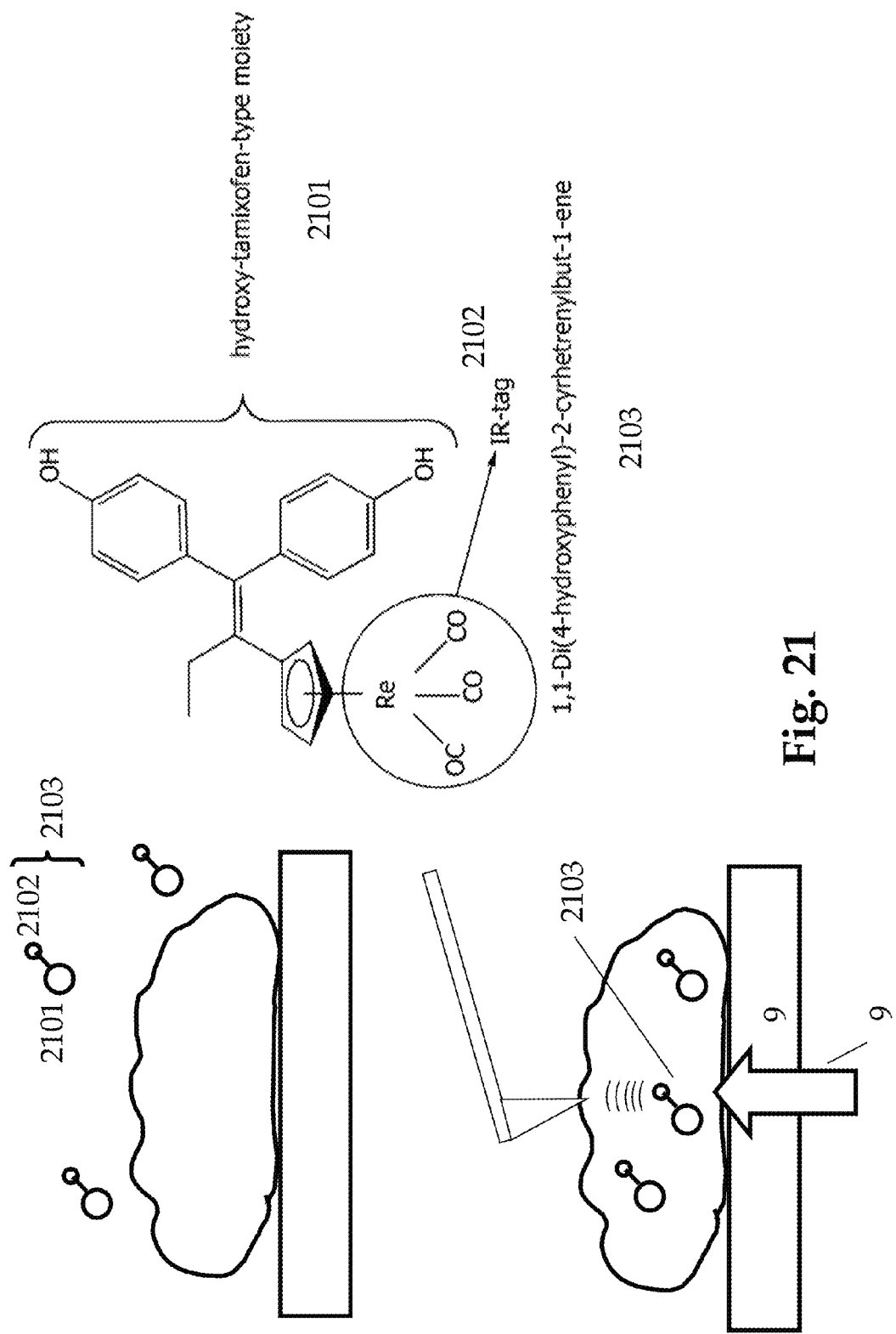
FIG. 21 shows a simplified schematic diagram for tagging a molecule with an IR absorbing tag.

As a proof of principle, the inventors have tested a transition-metal-carbonyl-labeled molecule, as shown in FIG. 21. A hydroxyl-tamixofen type moiety 2101 (i.e. a drug) was functionalized with an IR tag 2102, in this case a metal carbonyl. The resulting molecule 1,1-Di(4-hydroxyphenyl)-2-cyrhetrenylbut-1-ene is still small enough to enter cells and remains chemically active. But the addition of the IR tab 2101 allows it to be used to observe the uptake of the drug 2101 with sub-micron spatial resolution.

Figure 23:
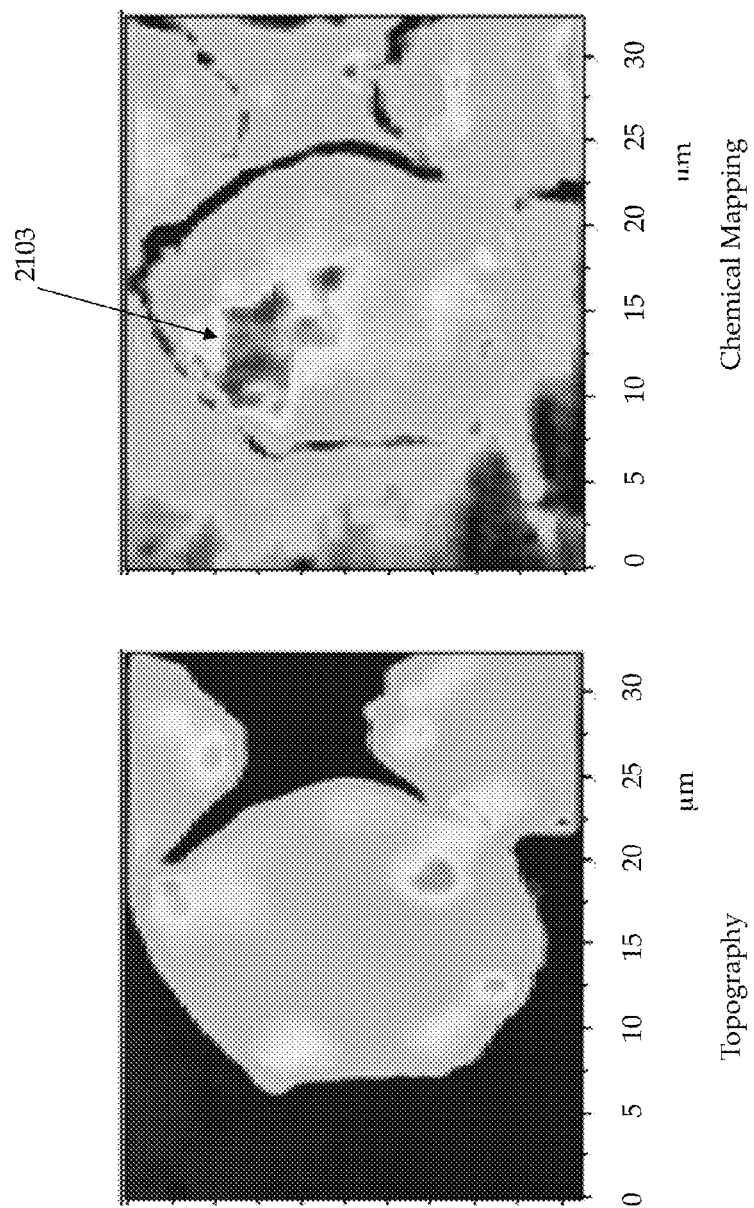
FIG. 23 shows example topographics and chemical imaging data of tagged molecules detected inside a cell using an IR absorbing tag.

To achieve this, the inventors incubated cells with the tagged molecule 2103. After washings, cells in suspension have been deposit and dried on the Zn—Se prisma. The preparation has been found to be stable for at least several weeks after preparation. The inventors have then set the IR source wavelength to an absorption band of the carbonyl group. An example of such a measurement is shown in FIG. 23 where the absorption band at 1904 $cm^{-1}$ was used to map the location of the tagged drug 2103 inside the cell. This technique provides thus the ability to map the spatial distribution of small molecules. The advantage of such IR-labels is their small size, in comparison to fluorescent probe for example. They can be used to label a molecule without affecting its physico-chemical properties and hence its function or behavior (including cell-penetration properties and cell-distribution). When a fluorescent probe is used to label a large molecule as a protein, its effect onto the physico-chemical characteristics of the protein can be neglected. But it is certainly not the case for small molecules as that tested by the inventors.

Example IR Tagging Protocol.

In one experiment, the inventors used MDA-MB-231 cells incubated with 1,1-Di(4-hydroxyphenyl)-2-cyrhetrenylbut-1-ene, whose molecular structure is shown in FIG. 21. An example protocol is described below. It is understood that many variations in this protocol can achieve suitable IR tagging.

Preparation of the Cell-Thin Layer on the ZnSe Prisma (a) Cells were seeded at a density so as to reach confluency after 24 h and incubated at 37° C. under an atmosphere of 95% air/5% $CO_2$ (human cells). Cells were washed with phosphate buffered saline (PBS), and fresh growth medium (6 mL) was added to each flask.

(b) The molecule was added as solutions in DMSO (60 mL, final DMSO concentration 1%). After an incubation in the presence of the molecule at 37° C. under an atmosphere of 95% air/5% $CO_2$ for a period of 1 h, the medium was removed and the flask was washed with PBS.

(c) Trypsin (0.25% in PBS) was added, and the cells were harvested after 5 min. The resulting suspension was centrifuged, and the supernatant discarded.

(d) The cell pellet was washed twice with saline (0.9% sodium chloride, 5 mL), and the supernatant discarded each time.

(e) At that stage, it is possible to estimate the number of cells by counting.

(f1) The cells pellet was deposit on a nitrocellulose membrane for an analysis by FTIR.

(f2) OR the cells were dispersed in 100 μL and deposit on the surface of the ZnSe prism as a drop. After settling down (15 min.) the supernatant was carefully sucked up and the residual thin layer was dried The layer of cells was kept under argon for several days before AFM-IR analysis Measurements can also be performed in liquid. This provides tremendous potential to map molecules on living biological systems, for example cells. In liquid the cantilever resonances are often significantly damped, but the inventors have demonstrated the ability to obtain spectra and maps under these conditions. The higher damping rates in fact enables more rapid IR laser pulses and faster measurement times.

It will be apparent to those skilled in the art that modifications may be made to embodiments described herein without departing from the spirit and scope of the invention. Other features not mentioned in the specification, but known to one skilled in the art may be integrated as well without departing from the spirit and scope of the present invention. In particular, many of the embodiments may be used independent of the PTIR technique with alternative embodiments of AFM-based IR spectroscopy or more generally in IR spectroscopy and imaging, all within the scope of the invention. The methods, system, and apparatuses of the present invention should therefore be afforded the broadest possible scope under examination. As such, the invention taught herein by specific examples is limited only by the scope of the claims that follow.

We claim:

1. A method for measuring a localized IR spectra of a sample comprising:
   interacting an AFM probe tip with a region of a sample;
   illuminating the sample with pulsed variable wavelength IR radiation at a pulse frequency
   collecting deflection data from the probe due to exciting a resonant oscillation of the probe in response to thermal expansion of the sample due to spectrally dependent absorption of radiation from the IR;
   applying a modulation signal to modulate the tip-sample interaction; and,
   using heterodyne techniques to measure the tip response due to IR absorption due to heterodyne mixing of the IR source pulse frequency and the tip modulation frequency, thereby reducing the effect of background forces not localized to the tip.

2. The method of claim 1 comprising operating the AFM in tapping mode.

* * * * *